United States Patent
Tasaka et al.

(10) Patent No.: US 6,306,853 B1
(45) Date of Patent: Oct. 23, 2001

(54) 1,4-DIHYDROPYRIDINE DERIVATIVES

(75) Inventors: Shigeyuki Tasaka; Akira Kiue; Hiromasa Omori, all of Omiya; Hirokazu Tanabe, Tokyo; Noriaki Gomi, Omiya, all of (JP)

(73) Assignee: Nikken Chemicals Co., Ltd., Tokyo (JP)

( * ) Notice: Subject to any disclaimer, the term of this patent is extended or adjusted under 35 U.S.C. 154(b) by 0 days.

(21) Appl. No.: 09/622,086

(22) PCT Filed: Feb. 3, 1999

(86) PCT No.: PCT/JP99/00458

§ 371 Date: Aug. 10, 2000

§ 102(e) Date: Aug. 10, 2000

(87) PCT Pub. No.: WO99/41250

PCT Pub. Date: Aug. 19, 1999

(30) Foreign Application Priority Data

Feb. 10, 1998 (JP) .................................. 10-042969
May 25, 1998 (JP) .................................. 10-198184

(51) Int. Cl.[7] .................. C07D 40/12; C07D 409/14; C07D 471/04; A61K 31/445; A61K 31/505

(52) U.S. Cl. .................. 514/235.5; 546/118; 546/256; 514/303; 514/333; 514/256; 514/253.01; 514/235.5; 544/333; 544/360; 544/131

(58) Field of Search .................. 546/118, 256; 514/303, 333, 256, 253.01, 235.5; 544/333, 360, 131

(56) References Cited

FOREIGN PATENT DOCUMENTS

| | | |
|---|---|---|
| 46-40625 | 12/1971 | (JP) . |
| 56-37225 | 8/1981 | (JP) . |
| 60-120861 | 6/1985 | (JP) . |
| 60-214786 | 10/1985 | (JP) . |
| 61-140567 | 6/1986 | (JP) . |
| 2-40383 | 2/1990 | (JP) . |
| 2-138221 | 5/1990 | (JP) . |
| 2-240081 | 9/1990 | (JP) . |
| 5-117235 | 5/1993 | (JP) . |
| 10 204061 | 8/1998 | (JP) . |
| WO 96/04268 | 2/1996 | (WO) . |
| WO 97/28125 | 8/1997 | (WO) . |
| WO 97/28152 | 8/1997 | (WO) . |

OTHER PUBLICATIONS

Takashi Tsuruo, et al., "Overcoming of Vincristine Resistance in P388 Leukemia in Vivo and in Vitro through Enhanced Cytotoxicity of Vincristine and Vinblastine by Verapamil" Cancer research, vol. 41, May 1981, pp. 1967–1972.

Takashi Tsuruo, "Therapeutic Approaches For Multidrug Resistance", Jpn. J. Cancer Chemother 15(10), Oct. 1988, pp. 2848–2852.

*Primary Examiner*—Mukund J. Shah
*Assistant Examiner*—Hong Liu
(74) *Attorney, Agent, or Firm*—Christie, Parker & Hale, LLP

(57) ABSTRACT

A 1,4-dihydropyridine derivative having the formula (I):

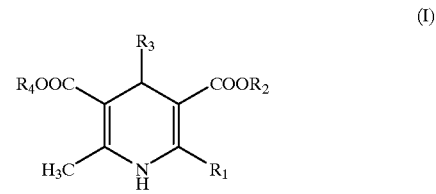

wherein, $R_1$ represents a substituted or unsubstituted phenyl or pyridyl group, $R_2$ represents a $C_1$ to $C_5$ lower alkyl group, $R_3$ represents a substituted or unsubstituted $C_1$ to $C_8$ alkyl, alkenyl, alkynyl or substituted or unsubstituted $C_3$ to $C_7$ cycloalkyl or cycloalkenyl group, $R_4$ represents —A—$R_5$, wherein A represents a $C_3$ to $C_5$ alkynylene group having one triple bond, and $R_5$ represents a substituted or unsubstituted pyridyl, quinolyl, isoquinolyl or pyrimidyl group and a drug for overcoming resistance to an anti-cancer drug or a drug increasing the effect of an anti-cancer drug containing as an effective ingredient the derivative or its pharmacologically acceptable salt or hydrate.

10 Claims, No Drawings

1,4-DIHYDROPYRIDINE DERIVATIVES

TECHNICAL FIELD

The present invention relates to a novel 1,4-dihydropyridine derivative having an action for overcoming resistance to an anti-cancer drug or an action for increasing the effect of an anti-cancer drug or a drug for overcoming resistance to an anti-cancer drug or a drug for increasing the effect of an anti-cancer drug having the derivative or its pharmacologically acceptable salt or hydrate as an effective ingredient.

BACKGROUND ART

Many compounds are already known as 1,4-dihydropyridine derivatives. The majority of these known 1,4-dihydropyridine derivatives have a pharmacological activity with respect to the circulatory system. For other pharmacological activities, there have been just a few reports for those having an anti-inflammatory action, liver protecting action, etc.

On the other hand, "acquired resistance", where the effect of the anti-cancer drug is lost during the treatment, is becoming a problem in the chemotherapy of cancers. Multidrug resistance which exhibited against a variety of anti-cancer drugs is becoming an important problem. As a method for overcoming this multidrug resistance, it has been reported that combined administration of an anti-cancer drug and some calcium antagonists (1,4-dihydropyridine compounds such as nicardipine) is effective (Cancer Res., 41, 1967–1972 (1981), Cancer and Chemotherapy, vol. 15, 2848 (1988)).

Further, Japanese Unexamined Patent Publication (Kokai) No. 2-40383, Japanese Unexamined Patent Publication (Kokai) No. 2-240081, describe a 1,4-dihydropyridine compound having a dioxene ring or a dithiene ring at its 4-position, Japanese Unexamined Patent Publication (Kokai) No. 5-117235 and Japanese Unexamined Patent Publication (Kokai) No. 2-138221 describes a 1,4-dihydropyridine compound having an aromatic group such as a phenyl group bonded at its 4-position, and WO96/04268, WO97/28125, WO97/28152 describe a 1,4-dihydropyridine compound having, an alkyl group etc., bonded at its 4-position, as those having an action for overcoming resistance to an anti-cancer drug.

However, the inventions described in the above references (i.e., Cancer Res., 41, 1967–1972 (1981) and Cancer and Chemotherapy, vol. 15, 2848 (1988)) use calcium antagonists for overcoming resistance to anti-cancer drugs and have the defect that they are not necessarily practical in terms of side effects. That is, calcium channel blockers inherently have a powerful action and act on the heart, blood vessels, etc. even in very small amounts, and therefore, if large amounts of these drugs are used, there is the problem that inconvenient effects are to be caused on the heart and circulatory system.

Further, among the 1,4-dihydropyridines described in the above references, Japanese Unexamined Patent Publication (Kokai) No. 2-40383, Japanese Unexamined Patent Publication (Kokai) No. 2-240081, WO96/04268, WO97/28125, WO97/28152 etc., there are preferable compounds having an action to increase the effect of anti-cancer drugs or an action for overcoming the resistance to an anti-cancer drug and further have almost no calcium channel blocking action. However, the chemical structures of the 1,4-dihydropyridine compounds described in these publications are clearly different from those of the present invention.

DISCLOSURE OF THE INVENTION

Therefore, an object of the present invention is to provide a novel 1,4-dihydropyridine derivative having an activity for overcoming resistance to an anti-cancer drug or an activity for increasing the effect of an anti-cancer drug.

In accordance with the present invention, there is provided a 1,4-dihydropyridine derivative having the formula (I):

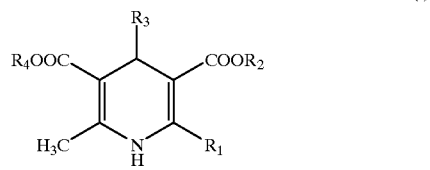

wherein $R_1$ represents a substituted or unsubstituted phenyl or pyridyl group, $R_2$ represents a $C_1$ to $C_5$ lower alkyl group, $R_3$ represents a substituted or unsubstituted $C_1$ to $C_8$ alkyl, alkenyl or alkynyl group, or substituted or unsubstituted $C_3$ to $C_7$ cycloalkyl or cycloalkenyl group, $R_4$ represents —A—$R_5$, wherein A represents a $C_3$ to $C_5$ alkynylene group having one triple bond, and $R_5$ represents a substituted or unsubstituted pyridyl, quinolyl, isoquinolyl or pyrymidyl group.

In accordance with the present invention, there is also provided a drug, particularly a drug for overcoming resistance to an anti-cancer drug or a drug for increasing the effect of an anti-cancer drug containing the 1,4-dihydropyridine derivative or its pharmacologically acceptable salt or hydrate.

BEST MODE FOR CARRYING OUT THE INVENTION

The present inventors synthesized 1,4-dihydropyridine derivatives having various substituents and screened a broad range of these compounds for combined effects with anti-cancer drugs. As a result, we found a novel compound, that is, a 1,4-dihydropyridine derivative having the formula (I) has the action for remarkably increasing the sensitivity of cancer calls to an anti-cancer drug, in particular, the sensitivity of acquiring resistant cancer cells to an anti-cancer drug (i.e., the action for overcoming resistance to anti-cancer drug). Further, we found that such compounds exhibit an effect for prolonging the survival days of a cancerous animal by the combined administration of an anti-cancer drug and further that there are almost no action for the calcium channel, and the toxicities are low, and thus the present invention has been completed.

The present invention will now be explained in further detail.

In the 1,4-dihydropyridine derivative having the formula (I), as $R_1$, a substituted or unsubstituted phenyl or heterocyclic group such as a pyridyl group may be mentioned. Preferably, a phenyl or pyridyl group, which may be substituted with a group selected from the group consisting of a 5- or 6-membered heterocyclic group, including a condensed heterocyclic group, having at least one nitrogen or sulfur atom and optionally substituted at the ring thereof, with a $C_1$ to $C_3$ lower alkyl group, trifluoromethyl group or halogen atom; a $C_1$ to $C_3$ lower alkylthio group; a $C_1$ to $C_3$ lower alkyloxy group; a $C_1$ to $C_3$ lower alkyl group; a two-substituted amino group; and a halogen atom may be mentioned. More preferably, a pyridyl group, or a phenyl group substituted with one heterocyclic group selected from the group consisting of imidazopyridine, piperadine, imidazole, morpholine, indole, benzimidazole, indazole, thiophene, and 1H-benzotriazole, provided that these heterocyclic groups may be substituted with a $C_1$ to $C_3$ lower alkyl group or trifluoromethyl, especially (2-substituted imidazo[4,5-c]pyridin-1-yl)phenyl group substituted, at the 2-position of the imidazo[4,5-c]pyridine, with a $C_1$ to $C_3$ lower alkyl or trifluoromethyl group, or a (1-imidazolyl) phenyl group may be mentioned.

Typically, $R_1$ is a 3-pyridyl, 4-(2-methylimidazo[4,5-b] pyridin-1-yl)phenyl,4-(2isopropylimidazo[4,5-c]pyridin-1-yl)phenyl,3-(2-methylimidazo[4,5-c]pyridin-1-yl)phenyl,3-(2-isopropylimidazo[4,5-c]pyridin-1-yl)phenyl,3-(2-trifluoromethylimidazo[4,5-c]pyridin-1-yl)phenyl, 4-(2-methylimidazo[4,5-c]pyridin-1-yl)phenyl,4-(4-methylpiperadin-1-yl)phenyl, 4methtylthiphenyl,4-(1H-benzotriazol-1-yl)phenyl,4-(benzoimidazoyl-1-yl)phenyl,4-(1-imidazolyl)phenyl,3-(1-imidazolyl)phenyl,4-morpholinophenyl,4-(1-indazolyl)phenyl,4-(3-thienyl) phenyl,3-(3-thienyl)phenyl, 4-(1-indolyl)phenyl, etc. may be mentioned.

As $R_2$, a $C_1$ to $C_5$ lower alkyl group, preferably, methyl or ethyl, may be mentioned.

As $R_3$, a substituted or unsubstituted $C_1$ to $C_8$ alkyl, alkenyl or alkynyl group or a substituted or unsubstituted $C_3$ to $C_7$ cycloalkyl group, or cycloalkenyl group. Preferably a $C_1$ to $C_6$ alkyl or alkenyl group; a $C_1$ to $C_4$ lower alkyl group or $C_2$ to $C_3$ lower alkenyl group substituted with a phenyl group, thienyl group, furyl group, cyclohexyl group, naphthyl group, indanyl group, 1,1a,6,10b-tetrahydrodibenzo[a,e]cyclopropa[c]cycloheptene-yl group, 5H-dibenzo[a,d]cycloheptene-yl group or 10,11-dihydro-5H-dibenzo[a,d]cycloheptene-yl group, provided that these groups may be substituted with a halogen atom, $C_1$ to $C_3$ lower alkyl group, trifluoromethyl group, substituted or unsubstituted $C_1$ to $C_3$ lower alkyloxy group; or $C_5$–$C_7$ cycloalkyl group may be mentioned. More preferably, a $C_1$ to $C_6$ alkyl or alkenyl group; $C_1$–$C_4$ lower alkyl or $C_2$–$C_3$ lower alkenyl group substituted with thienyl group or phenyl group, (phenyl group may be substituted with a halogen atom, $C_1$ to $C_3$ lower alkyl group, trifluoromethyl group, $C_1$ to $C_3$ lower alkyloxy group, or $C_1$ to $C_3$ lower alkyloxy group) or thienyl group; or cyclohexyl group, etc. may be mentioned.

Typically, methyl, n-pentyl, n-butyl, 2,2-dimethylpropyl, octyl group; 2-methylthioethyl group; benzyl, benzhydryl, phenetyl, 1-phenylethyl, 3-phenylpropyl, 2-phenylpropyl, 4-phenylbutyl, 2-phenylethenyl, 2-phenyl-1-propenyl, 2,2-diphenylethenyl, phenylethynyl group, provided that these groups may be substituted, at the benzene ring thereof, with a chlorine atom, fluorine atom, methyl, ethyl, isopropyl, methoxy, cyclopentylmethyloxy, 2-(4-fluorophenyl) ethyloxy or 2-(5-thiazolyl)ethyloxy group, etc; 2-(3-thienyl) ethyl, 2-(2-furyl)ethyl, 2-(2-furyl)ethenyl, 2-cyclohexylethenyl, 3-cyclohexylpropyl, 2-indanylmethyl, 2-(2-naphthyl)ethyl, 1,1-difluoro-1,1a,6, 10b-tetrahydrodibenzo[a,e]cyclopropa[c]cyclohepten-6-ylmethyl or 1,1-difluoro-1,1a,6,10b -tetrahydrodibenzo[a,e] cyclopropa[c]cyclohepten-6-ylidenemethyl, 5H-dibenzo[a,d]cyclohepten-5-ylmethyl or 10,11-dihydro-5H-dibenzo[a,d]cyclohepten-5-ylmethyl group; cyclohexyl group, etc. may be mentioned.

$R_4$ represents —A—$R_5$, wherein A represents a $C_3$ to $C_5$ alkynylene group, having one triple bond and $R_5$ represents a substituted or unsubstituted pyridyl, quinolyl, isoquinolyl or pyrimidyl group. Preferably, $R_5$ is a 3-pyridyl, 3-quinolyl, 4-isoquinolyl or 5-pyrimidyl group, provided that these groups may be substituted with methyl, ethyl, methoxy group, a halogen atom, etc. Especially preferably, A is propynylene, 1-methyl-2-propynylene, or butynylene group, etc., and $R_5$ is a 3-pyridyl, 3-quinolyl, 4-isoquinolyl or 5-pyrimidyl group, etc.

In the present invention, as specifically preferable compounds, all of the compounds shown in the Examples may be mentioned.

The 1,4-dihydropyridine derivative having the formula (I) provided by the present invention may be produced by a known method used for the production of a 1,4-dihydropyridine derivative in the past.

That is, the compound having the formula (I) may be produced by a reaction of an aldehyde having the formula (II) and an acylacetate ester having the formula (III) and 3-aminocrotonate ester having the formula (IV) in the presence or absence of an organic solvent:

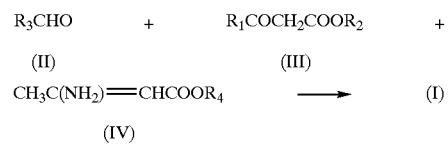

wherein $R_1$, $R_2$, $R_3$ and $R_4$ are the same as defined in the formula (I).

The reactions used in these production methods are basically the same as the known methods for the production of a 1,4-dihydropyridine derivative in the past (e.g., the methods described in Japanese Examined Patent Publication (Kokoku) No. 46-40625 and No. 56-37225, Japanese Unexamined Patent Publication (Kokai) No. 60-214786, etc.). Therefore, the 1,4-dihydropyridine derivative of the present invention may be produced by the above methods, and also produced by suitably applying a different reaction described in these known references. The starting materials used for these methods can be readily obtained or produced by a person skilled in the art depending upon the need. For example, an acylacetate ester may be produced by a reaction with acetophenones and carbonates. Further, a 3-aminocrotonate ester may be produced by the reaction of ammonia gas with the above acetoacetate ester. An aldehyde can be readily produced by a known method widely used, that is, the reduction of an ester or the oxidation of an alcohol.

A compound having the formula (I) obtained by this method can be isolated and purified by a known treatment means (e.g., extraction, chromatography, recrystallization, etc.)

The 1,4-dihydropyridine derivative having the formula (I) has asymmetric carbon atoms, and therefore, have optical isomers. The present invention includes all optical isomers and mixtures thereof. Further, the mixtures of isomers may be separated into the chiral isomers depending upon the need by a separated crystallization or chromatography.

The compound according to the present invention exhibits an action for increasing the effect of an anti-cancer drug and exhibits an action for overcoming the resistance to anti-cancer drugs for an adriamycin resistant cancer, vincristine resistant cancer or etoposide resistant cancer and prolongs the survival days of a cancerous animal by the combined administration of an anti-cancer drugs, and therefore, is useful as a drug for overcoming resistance to an anti-cancer drug or drug for increasing the effect of an anti-cancer drug.

When the compound according to the present invention is used as a drug for overcoming resistance to an anti-cancer drug or a drug for increasing the effect of an anti-cancer drug, it may be administered by a suitable method such as oral or nonoral administration. As a form of oral administration are tablets, granules, capsules, pills, dispersions, liquids, etc. Further as a form of non-oral administration are injections, suppositories, etc. These may be prepared according to ordinary methods using the present compound or its pharmacologically acceptable salt with a usual preparation carrier.

In the case of oral administration, the preparations can be prepared into the desired form using an excipient such as lactose, glucose, corn starch, sucrose, a disintegrator such as calcium carboxymethylcellulose, hydroxypropylcellulose, a lubricant such as calcium stearate, magnesium stearate, talc, polyethylene glycol, hardened oil, a binder such as hydroxypropylcellulose, hydroxypropylmethylcellulose, carboxymethylcellulose, polyvinyl alcohol, gelatin, arabia gum, a humectant such as glycerin, ethylene glycol, and, in addition, if necessary, a surfactant, a corrigent, etc.

In the case of a non-oral drug, a diluent such as water, ethanol, glycerol, propylene glycol, polyethylene glycol, a vegetable oil, agar, tragacanth gum may be used and, optionally, a solution adjuvant, a suspending agent, an emulsifying agent, a stabilizer, a buffer agent, an isotonicity, a preservative, a soothing agent, etc. may be used.

When formulating the present compound as a drug for overcoming resistance to an anti-cancer drug or a drug for increasing the effect of an anti-cancer drug, the dosage, as the present compound, is per adult, in the case of oral administration, 5 to 1000 mg per day, preferably 5 to 200 mg, and in the case of non-oral administration, 1 to 500 mg per day, preferably 1 to 200 mg. The desired effect of treatment can be expected by administration divided into one to three dosages per day.

EXAMPLES

The following Synthesis Examples, Preparation Examples, and Test Examples of the compounds according to the present invention will now be explained as Examples.

Synthesis Examples

Synthesis Examples are shown below. The NMR data shows the signals of $^1$H-NMR measured by a $CDCl_3$ solvent.

Reference Example 1

Synthesis of 3-aminocrotonate 3-(3-pyridyl)-2-propynylester 25.8 g of 3-bromopyridine, 3.47 g of 10% palladium-activated carbon (Pd—C), 3.41 g of triphenyl phosphine, 56.4 g of potassium carbonate and 1.24 g of copper iodide were dissolved in 250 ml of 50% aqueous dimethoxyethane solution, followed by stirring at room temperature for 30 minutes. Then, 22.9 g of propargyl alcohol was added thereto, followed by heating at 80° C. for 16 hours under stirring. After cooling, the insolubles were removed, the dimethoxyethane was distilled off in vacuo. Thereafter, the resultant mixture was acidified by adding hydrochloric acid and, after washing with toluene, the mixture was alkanized again with the addition of potassium carbonate, followed by extracting with ethyl acetate. The extract thus obtained was purified by column chromatography to obtain 19.6 g (90%) of 1-(3-pyridyl)-1-propyn-3-ol. Then, 19.6 g of the 1-(3-pyridyl)-1-propyn-3-ol obtained above and 72 mg of 4-dimethylamino pyridine were dissolved in 150 ml of tetrahydrofuran and 14.8 g of diketene was added thereto at 0° C., followed by stirring at room temperature for 2 hours. After the solvent was distilled off in vacuo, the resultant product was extracted with ethyl acetate to obtain 3-(3-pyridyl)-2-propynyl ester. Then, this compound was dissolved, without purification, in 500 ml of tetrahydrofuran, followed by blowing gaseous ammonia thereto at 0° C. for 4 hours. After allowing to stand at room temperature for 3 days, the solvent was distilled off in vacuo and the residue was purified with Florisil (magnesium silicate manufactured by Florisine to obtain the target compound in an amount of 22.2 g (73%).

NMR: 1.93(3H,s), 5.49(1H,s), 4.90(2H,s), 7.23(1H,m), 7.72(1H,m), 8.51(1H,q), 8.67(1H,d)

Reference Example 2

The following compounds were synthesized according to a method similar to Reference Example 1.
3-Aminocrotonate 3-(3-quinolyl)-2-propynyl ester
NMR: 1.95(3H,s), 4.63(1H,s), 4.97(3H,s), 7.57(1H,t), 7.73(1H,t), 7.78(1H,d), 8.08(1H,d), 8.26(1H,d), 8.92(1H,d)
3-Aminocrotonate 3-(4-isoquinolyl)-2-propynyl ester
NMR: 1.95(3H,s), 4.65(1H,s), 5.05(3H,s), 7.65(1H,t), 7.78(1H,t), 7.98(1H,d), 8.25(1H,d), 8.69(1H,s), 9.18(1H,s)
3-Aminocrotonate 3-(5-pyrimidyl)-2-propynyl ester
NMR: 1.95(3H,s), 4.60(1H,s), 4.92(2H,s), 8.78(2H,s), 9.13(1H,s) 3-Aminocrotonate 1-methyl-3-(3-pyridyl)-2-propynyl ester
NMR: 1.59(3H,d), 1.93(3H,s), 4.58(1H,s), 5.71(1H,q), 7.23(1H,m), 7.72(1H,m), 8.51(1H,d), 8.67(1H,d)
3-Aminocrotonate 4-(3-pyridyl)-3-butynyl ester
NMR: 1.92(3H,s), 2.77(2H,t), 4.26(2H,t), 4.57(1H,s), 7.22(1H,dd), 7.68(1H,dt), 8.49(1H,dd), 8.63(1H,d)

Reference Example 3

Synthesis of 1,1-difluoro-6-formylmethylidene-1,1a,6,10b-tetrahydrodibenzo[a,e]cyclopropar[c]cycloheptene 860 mg of sodium hydride was added to 70 ml of toluene and then 4.3 ml of ethyl diethylphosphonoacetate was dropwise added at 0° C. After stirring at room temperature for 1 hour, a 40 ml benzene solution of 5.00 g of 1,1-difluoro-1,1a,6,10b-tetrahydrodibenzo[a,e]cyclopropa[c]cycloheptene was dropwise added thereto at 0° C., followed by stirring at 100° C. for 2 hours. After cooling, water was added and the resultant mixture was extracted with ethyl acetate and the extract was purified by column chromatography to obtain 3.99 g (63%) of the unsaturated ester. 3.99 g of the ester was dissolved in 70 ml of dichloromethane and, after cooling at −78° C., a 28.2 ml of 0.95 M n-hexane solution of hydrogenated diisobutyl aluminum was dropwise added thereto. After the resultant mixture was stirred for 2 hours at −78° C. and for 1 hour at room temperature, methanol and then 10% aqueous sodium hydroxide solution were added. The organic layer was separated and distilled off in vacuo to obtain the allylalcohol product. This compound was dissolved in 150 ml of dichloromethane, without purification, and 18 g of manganese dioxide was added, followed by stirring at room temperature for 4 hours. After removing the insolubles and distilling off the solvent in vacuo, the product was purified by a column chromatography to obtain the target product in an amount of 3.06 g (89%).

Reference Example 4

Synthesis of 1,1-difluoro-6-formylmethyl-1,1a,6,10b-tetrahydrodibenzo[a,e]cyclopropa[c]cycloheptene 2.17 g of 6-ethoxycarbonylmethylidene-1,1-difluoro-1,1a,6,10b-tetrahydrodibenzo[a,e]cyclopropa[c]cycloheptene was dissolved in 50 ml of methanol-dichloromethane (1:1) and 0.5 ml of acetic acid and 300 mg of 10% palladium-activated carbon black (Pd—C) were added thereto, followed by stirring at room temperature for 48 hours under hydrogen atmosphere. After removing the insolubles, the solvent was distilled off in vacuo to obtain the saturated alcohol.

25 ml of tetrahydrofuran was added to 505 mg of aluminum lithium hydride at 0° C. and, then, a 25 ml tetrahydrofuran solution of the above saturated alcohol at 0° C., followed by stirring for 15 minutes at 0° C. and for 2 hours at room temperature. Thereafter, 0.25 ml of water, 0.4 ml of a 10% aqueous sodium hydroxide solution and 0.8 ml of water were added thereto in this order all at 0° C., followed by stirring for 30 minutes. After removing the insolubles, the solvent was distilled off in vacuo to obtain alcohol product.

0.8 ml of oxalyl chloride was dissolved in 20 ml of dichloromethane and, after dropwise adding 5 ml of a dichloromethane solution of 1.3 ml of dimethylsulfoxide at −78° C., the mixture was stirred for 2 minutes, followed by dropwise adding a 15 ml dichloromethane solution of the above alcohol product at −78° C. for 15 minutes. Furthermore, 3.7 ml of triethylamine was dropwise added at −78° C., followed by stirring for 5 minutes and, then, temperature was increased to room temperature. To this reaction mixture, water was added, followed by extracted with dichloromethane, and the extract was purified by column chromatography to obtain the target product in an amount of 927 mg (74%).

Example 1

Synthesis of 4,6-dimethyl-2-[4-(2-methylimidazo[4,5-c]pyridin-1-yl)phenyl]-1,4-dihydropyridin-3,5-dicarboxylic acid 3-ethylester 5-[3-(3-pyridyl)-2-propynyl]ester (Compound 1)

611 mg of ethyl 4-(2-methylimidazo[4,5-c]pyridin-1 -yl)benzoyl acetate, 409 mg of 3-aminocrotonate 3-(3-pyridyl)-2-propynyl ester and 167 mg of acetaldehyde were heated and refluxed in 10 ml of ethanol for 6 hours. After the reaction, the reaction solution was concentrated to dryness in vacuo and the oily substance was purified by silica gel column chromatography to obtain the target compound in an amount of 566 mg (55.0%).

NMR: 1.03(3H,t), 1.21(3H,d), 2.41(3H,s), 2.58(3H,s), 4.02(2H,m), 4.07(1H,q), 5.04(2H,q), 7.08(1H,d), 7.26(1H, t), 7.39(2H,d), 7.56(2H,d), 7.76(1H,dt), 8.32(1H,d), 8.55(1H,dd), 8.71(1H,d), 9.05(1H,s)

Example 2

Synthesis of 4-(2, 2-dimethylpropyl)-6-methyl-2-[4-(2-methylimidazo[4,5-c]pyridin-1-yl)phenyl]-1,4-dihydropyridin-3,5-dicarboxylate 3-ethylester 5-[3-(3-pyridyl)-2-propynyl]ester (Compound 2)

514 mg of ethyl 4-(2-methylimidazo[4,5-c]pyridin-1-yl)benzoylacetate, 314 mg of 3-aminocrotonate 3-(3-pyridyl)-2-propynylester and 319 mg of 3,3-dimethylbutylaldehyde were heated and refluxed in 10 ml of ethanol for 33 hours. Thereafter, the temperature was cooled to room temperature and 735 mg of ammonium acetate was added thereto, followed by further heating and refluxing for 9 hours. After the reaction, the reaction solution was concentrated to dryness in vacuo and dissolved in 5 ml of ethyl acetate. The insolubles were removed by filtration and the solvent was concentrated to dryness. The oily substance was purified by silica gel column chromatography to obtain the target compound in an amount of 296 mg (30.8%).

NMR: 1.02(9H,s), 1.07(3H,t), 2.46(3H,s), 2.58(3H,s), 4.03(2H,m), 4.30(1H,t), 5.05(2H,q), 7.09(1H,d), 7.27(1H,t), 7.38(2H,d), 7.58(2H,d), 7.75(1H,dt), 8.31(1H,d), 8.55(1H, dd), 8.69(1H,d), 9.04(1H,s)

The compounds of the following Examples synthesized on Example 1 or Example 2 will now be given together with the materials used and the NMR data. Further, the compounds were purified by recrystallizing with a suitable solvent or by silica gel column chromatography if necessary.

Since Examples 3 to 17 below used, as the starting materials, the same starting compounds (i.e., ethyl 4-(2-methylimidazo[4,5-c]pyridin-1-yl)benzoyl acetate and 3-aminocrotonate 3-(3-pyridyl)-2-propynylester), except for the aldehyde, as in Example 1, these starting compounds were not mentioned hereinbelow.

Example 3

6-Methyl-2-[4-(2-methylimidazo[4,5-c]pyridin-1-yl)phenyl]-4-pentyl-1,4-dihydropyridin-3,5-dicarboxylate 3-ethylester 5-[3-(3-pyridyl)-2-propynyl]ester (Compound 3)

Starting material: Capronaldehyde

NMR: 0.87(3H,t), 1.04(3H,t), 1.20–1.41(8H,m), 1.53(2H, m), 2.43(3H,s), 2.58(3H,s), 4.02(2H,m), 4.15(1H,t), 5.03 (2H,q), 7.08(1H,d), 7.27(1H,t), 7.39(2H,d), 7.56(2H,d), 7.76 (1H,dt), 8.32(1H,d), 8.55(1H,dd), 8.70(1H,d), 9.04(1H,s)

Example 4

4-Cyclohexyl-6-methyl-2-[4-(2-methylimidazo[4,5-c]pyridin-1-yl )phenyl]-1,4-dihydropyridin-3,5-dicarboxylate 3-ethylester 5-[3-(3-pyridyl)-2-propynyl]ester (Compound 4)

Starting material: Cyclohexane carboxyaldehyde

NMR: 1.04(3H,t), 1.05–1.80(11H,m), 2.43(3H,s), 2.58 (3H,s), 4.01(2H,m), 4.13(1H,t), 5.03(2H,q), 7.08(1H,d), 7.27(1H,t), 7.39(2H,d), 7.58(2H,d), 7.76(1H,dt), 8.32(1H, d), 8.55(1H,dd), 8.70(1H,d), 9.04(1H,s)

Example 5

6-Methyl-2-[4-(2-methylimidazo[4,5-c]pyridin-1-yl)phenyl]-4-(2-methylthioethyl)-1,4-dihydropyridin-3,5-dicarboxylate 3-ethylester 5-[3-(3-pyridyl)-2-propynyl]ester (Compound 5)

Starting material: 3-Methylthiopropanal

NMR: 1.03(3H,t), 1.88(2H,m), 2.10(3H,s), 2.45(3H,s), 2.58(3H,s), 2.59(2H,m), 4.02(2H,m), 4.23(1H,t), 5.04(2H, q), 7.08(1H,d), 7.26(1H,t), 7.39(2H,d), 7.57(2H,d), 7.79(1H, dt), 8.31(1H,d), 8.55(1H,dd), 8.71(1H,d), 9.04(1H,s)

Example 6

4-Benzyl-6-methyl-2-[4-(2-methylimidazo[4,5-c]pyridin-1-yl)phenyl]-1,4-dihydropyridin-3,5-dicarboxylate 3-ethylester 5-[3-(3-pyridyl)-2-propynyl]ester (Compound 6)

Starting material: Phenylacetaldehyde

NMR: 1.03(3H,t), 2.29(3H,s), 2.56(3H,s), 2.85(2H,d), 3.96(2H,m), 4.46(1H,t), 4.96(2H,q), 7.06(1H,d), 7.19–7.28 (6H,m), 7.34(2H,d), 7.42(2H,d), 7.76(1H,dt), 8.30(1H,d), 8.55(1H,dd), 8.71(1H,d), 9.02(1H,s)

Example 7

6-Methyl-4-(α-methylbenzyl)-2-[4-(2-methylimidazo[4,5-c]pyridin-1-yl)phenyl]-1,4-dihydropyridin-3,5-dicarboxylate 3-ethylester 5-[3-(3-pyridyl)-2-propynyl]ester (Compound 7)

Starting material: 2-Phenylpropanal

NMR: 0.99(1.5H,t), 1.05(1.5H,t), 1.36(1.5H,d), 1.38(1.5H,d), 2.33(1.5H,s), 2.35(1.5H,s), 2.57(1.5H,s), 2.99(1H,m), 3.91(2H,m), 4.51(1H,m), 4.83(2H,q), 7.07(0.5H,d), 7.08(0.5H,d), 7.15–7.30(6H,m), 7.34(1H,d), 7.36(1H,d), 7.46(1H,d), 7.48(1H,d), 7.75(1H,m), 8.30(0.5H,d), 8.32(0.5H,d), 8.55(1H,m), 8.70(0.5H,d), 8.71(0.5H,d), 9.03(1H,s)

Example 8

4-[(E)-2-cyclohexylethenyl]-6-methyl-2-[4-(2-methylimidazo[4,5-c]pyridin-1-yl)phenyyl]-1,4-dihydropyridin-3,5-dicarboxylate 3-ethylester 5-[3-(3-pyridyl)-2-propynyl]ester (Compound 8)

Starting material: (E)-3-Cyclohexylpropenal

NMR: 1.05(3H,t), 1.06–2.01(11H,m), 2.45(3H,s), 2.56(3H,s), 4.01(2H,m), 4.60(1H,d), 5.01(2H,q), 5.48(2H,m), 7.02(1H,d), 7.25(1H,m), 7.34(2H,d), 7.56(2H,d), 7.76(1H,dt), 8.18(1H,d), 8.54(1H,dd), 8.69(1H,d), 8.98(1H,s)

Example 9

6-Methyl-2-[4-(2-methylimidazo[4,5-c]pyridin-1-yl)phenyl]-4-(2-phenylethyl)-1,4-dihydropyridin-3,5-dicarboxylate 3-ethylester 5-[3-(3-pyridyl)-2-propynyl]ester (Compound 9)

Starting material: 3-Phenylpropanal

NMR: 1.03(3H,t), 1.91(2H,m), 2.45(3H,s), 2.58(3H,s), 2.75(2H,m), 4.02(2H,m), 4.28(1H,t), 5.04(2H,q), 7.06(1H,d), 7.16(1H,t), 7.21(2H,t), 7.24(2H,d), 7.37(2H,d), 7.53(2H,d), 7.71(1H,dt), 8.27(1H,d), 8.54(1H,dd), 8.68(1H,d), 9.03(1H,s)

Example 10

6-Methyl-2-[4-(2-methylimidazo[4,5-c]pyridin-1-yl)phenyl]-4-[(E)-2-phenylethenyl]-1,4-dihydropyridin-3,5-dicarboxylate 3-ethylester 5-[3-(3-pyridyl)-2-propynyl]ester (Compound 10) Starting material: Cinnamaldehyde NMR: 1.04(3H,t), 2.48(3H,s), 2.58(3H,s), 4.03(2H,m), 4.85(1H,d), 5.03(2H,q), 6.33(1H,dd), 6.46(1H,d), 7.09(1H,d), 7.20–7.29(4H,m), 7.37(2H,d), 7.41(2H,d), 7.60(2H,d), 7.65(1H,dt), 8.33(1H,d), 8.54(1H,dd), 8.65(1H,d), 9.05(1H,s)

Example 11

4-[2-(2-Chlorophenyl)ethyl]-6-methyl-2-[4-(2-methylimidazo[4,5-c]pyridin-1-yl)phenyl]-1,4-dihydropyridin-3,5-dicarboxylate 3-ethylester 5-[3-(3-pyridyl)-2-propynyl]ester (Compound 11)

Starting material: 3-(2-Chlorophenyl)propanal

NMR: 1.04(3H,t), 1.87(2H,m), 2.46(3H,s), 2.59(3H,s), 2.86(2H,m), 4.03(2H,m), 4.30(1H,t), 5.04(2H,q), 7.09(1H,d), 7.14(2H,m), 7.24(2H,m), 7.30(1H,d), 7.40(2H,d), 7.60(2H,d), 7.72(1H,dt), 8.32(1H,d), 8.54(1H,dd), 8.68(1H,d), 9.04(1H,s)

Example 12

4-[(E)-2-(2-chlorophenyl)ethenyl]-6-methyl-2-[4-(2-methylimidazo[4,5-c]pyridin-1-yl)phenyl]-1,4-dihydropyridin-3,5-dicarboxylate 3-ethylester 5-[3-(3pyridyl)-2-propynyl]ester (Compound 12)

Starting material: 2'-Chrolocinnamaldehyde

NMR: 1.05(3H,t), 2.47(3H,s), 2.59(3H,s), 4.03(2H,m), 4.88(1H,d), 5.06(2H,q), 6.34(1H,dd), 6.87(1H,d), 7.09(1H,d), 7.15(2H,t), 7.23(1H,dd), 7.31(1H,d), 7.41(2H,d), 7.56(1H,d), 7.64(2H,d), 7.70(1H,dt), 8.33(1H,d), 8.53(1H,dd), 8.67(1H,d), 9.05(1H,s)

Example 13

4-[2-(2-methoxyphenyl)ethyl]-6-methyl-2-[4-(2-methylimidazo[4,5-c]pyridin-1-yl)phenyl]-1,4-dihydropyridin-3,5-dicarboxylate 3-ethylester 5-[3-(3-pyridyl)-2-propynyly]ester (Compound 13)

Starting material: 3-(2-Methoxyphenyl)propanal

NMR: 1.05(3H,s), 1.85(2H,m), 2.44(3H,s), 2.59(3H,s), 2.74(2H,m), 3.78(3H,s), 4.03(2H,m), 4.28(1H,t), 5.03(2H,q), 6.84(2H,m), 7.10(1H,d), 7.15(1H,t), 7.23(2H,m), 7.40(2H,d), 7.59(2H,d), 7.71(1H,dt), 8.35(1H,d), 8.53(1H,dd), 8.67(1H,d), 9.05(1H,s)

Example 14

4-[(E)-2-(2-Methoxyphenyl)ethenyl]-6-methyl-2-[4-(2-methylimidazo[4,5-c]pyridin-1-yl)phenyl]-1,4-dihydropyridin-3,5-dicarboxylate 3-ethylester 5-[3-(3-pyridyl)-2-propynyl]ester (Compound 14)

Starting material: 2'-Methoxycinnamaldehyde

NMR: 1.07(3H,t), 2.45(3H,s), 2.59(3H,s), 3.79(3H,s), 4.03(2H,m), 4.85(1H,d), 5.04(2H,q), 6.32(1H,dd), 6.87(1H,dd), 7.10(1H,d), 7.16–7.23(4H,m), 7.41(2H,d), 7.47(1H,dd), 7.63(2H,d), 7.67(1H,dt), 8.35(1H,d), 8.54(1H,dd), 8.66(1H,d), 9.06(1H,s)

Example 15

4-[2-(2-Furyl)ethyl]-6-methyl-2-[4-(2-methylimidazo[4 5-c]pyridin-1-yl)phenyl]-1,4-dihydropyridin-3,5-dicarboxylate 3-ethylester 5-[3-(3-pyridyl)-2-propynyl]ester (Compound 15)

Starting material: 3-(2-Furyl)propanal

NMR: 1.02(3H,s), 1.93(2H,m), 2.44(3H,s), 2.58(3H,s), 2.77(2H,m), 4.01(2H,m), 4.28(1H,t), 5.03(2H,q), 6.27(2H,m), 7.08(1H,d), 7.24–7.28(4H,m), 7.39(2H,d), 7.56(2H,d), 7.75(1H,dt), 8.32(1H,d), 8.54(1H,dd), 8.69(1H,d), 9.04(1H,s)

Example 16

4-[(E)-2-(2-Furyl)ethenyl]-6-methyl-2-[4-(2-methylimidazo[4,5c] pyridin-1-yl)phenyl]1,4-dihdropyridin-3,5-dicarboxylate 3-ethylester 5-[3-(3-pyridyl)-2-propynyl]ester (Compound 16)

Starting material: (E)-3-(2-Furyl)propenal

NMR: 1.04(3H,s), 2.46(3H,s), 2.59(3H,s), 4.03(2H,m), 4.82(1H,d), 5.03(2H,q), 6.18(1H,d), 6.27(1H,d), 6.29(1H,s), 6.35(1H,dd), 7.09(1H,d), 7.23–7.27(4H,m), 7.41(2H,d), 7.60(2H,d), 7.71(1H,dt), 8.35(1H,d), 8.54(1H,dd), 8.67(1H,d), 9.05(1H,s)

Example 17

6-Methyl-2-[4-(2-methylimidazo[4,5-c]pyridin-1-yl)phenyl]-4-[2-(3-thienyl)ethyl]-1,4-dihydropyridin-3,5-dicarboxylate 3-ethylester 5-[3-(3-pyridyl)2-propynyl]ester (Compound 17)

Starting material: 3-(3-thienyl)propanal

NMR: 1.02(3H,s), 1.93(2H,m), 2.45(3H,s), 2.58(3H,s), 2.77(2H,m), 4.01(2H,m), 4.28(1H,t), 5.03(2H,q), 6.95(1H, dd), 6.97(1H,m), 7.07(1H,d), 7.22(2H,dd), 7.23(1H,s), 7.25 (1H,m), 7.38(2H,d), 7.55(2H,d), 7.72(1H,dt), 8.29(1H,m), 8.54(1H,dd), 8.68(1H,d), 9.03(1H,s)

Example 18

6-Methyl-2-[4-(2-methylimidazo[4,5-c]pyridin-1-yl) phenyl]-4-(2-phenylethyl)-1,4-dihydropyridin-3,5-dicarboxylate 3-ethylester 5-[3-(3-quinolyl)-2-propynyl]ester (Compound 18)

Starting material:

Ethyl 4-(2-methylimidazo[4,5-c]pyridin-1-yl) benzoylacetate

3-Aminocrotonate 3-(3-quinolyl)-2-propynylester

3-Phenylpropanal

NMR: 1.03(3H,t), 1.94(2H,m), 2.46(3H,s), 2.58(3H,s), 2.77(2H,m), 4.03(2H,m), 4.31(1H,t), 5.09(2H,q), 7.08(1H, d), 7.14(1H,m), 7.22(2H,t), 7.24(2H,m), 7.39(2H,d), 7.54 (2H,d), 7.56(1H,t), 7.72(2H,d), 8.09(1H,d), 8.22(1H,d), 8.31 (1H,d), 8.92(1H,d), 9.04(1H,s)

Example 19

6-Methyl-2-[4-(2-methylimidazo[4,5-c]pyridin-1-yl) phenyl]-4-[(E)-2-(2-phenyl)ethenyl]-1,4-dihydropyridin-3,5-dicarboxylate 3-ethylester 5-[(3-quonolyl)-2-propynyl]ester (Compound 19)

Starting material

The same as in Example 18, except that cinnamaldehyde was used as the aldehyde.

NMR: 1.04(3H,t), 2.51(3H,s), 2.56(3H,s), 4.02(2H,m), 4.88(1H,d), 5.09(2H,q), 6.35(1H,dd), 6.49(1H,d), 7.03(1H, d), 7.16(1H,t), 7.24(2H,t), 7.35(2H,d), 7.37(2H,t), 7.55(1H, t), 7.59(2H,d), 7.73(2H,m), 8.08(1H,d), 8.17(1H,d), 8.23 (1H,d), 8.89(1H,d), 9.00(1H,s)

Example 20

6-Methyl-2-[4-(2-methylimidazo[4,5-c]pyridin-1-yl) phenyl]-4-[(E)-2-(2-phenyl)ethenyl]-1,4-dihydropyridin-3,5-dicarboxylate 3-ethylester 5-[(3-isoquinolyl)-2-propynyl]ester (Compound 20)

Starting material

Ethyl 4-(2-methylimidazo[4,5-c]pyridin-1-yl) benzoylacetate

3-Aminocrotonate 3-(4-isoquinolyl)-2-propynylester Cinnamaldehyde

NMR: 1.03(3H,t), 2.53(3H,s), 2.55(3H,s), 4.01(2H,m), 4.90(1H,d), 5.17(2H,q), 6.36(1H,dd), 6.49(1H,d), 6.99(1H, d), 7.10(1H,t), 7.20(2H,t), 7.32(2H,d), 7.34(2H,d), 7.59(2H, d), 7.63(1H,t), 7.71(1H,t), 7.97(1H,d), 8.14(1H,d), 8.23(1H, d), 8.65(1H,s), 8.98(1H,s), 9.17(1H,s)

Example 21

4-[(E)-2-(2-chlorophenyl)ethenyl]-6-methyl-2-[4-(2-methylimidazo[4,5-c]pyridin-1-yl)phenyl]-1,4-dihydropyridin-3,5-dicarboxylate 3-ethylester 5-[(5-pyrimidyl)-2-propynyl]ester (Compound 21)

Starting material

Ethyl 4-(2-methylimidazo[4,5-c]pyridin-1-yl) benzoylacetate

3-Aminocrotonate 3-(5-pyrimidyl)-2-propenylester

2-Chlorocinnamaldehyde

NMR: 1.05(3H,t), 2.49(3H,s), 2.58(3H,s), 4.03(2H,m), 4.88(1H,d), 5.06(2H,q), 6.33(1H,dd), 6.87(1H,d), 7.06(1H, d), 7.15(2H,t), 7.30(1H,t), 7.31(1H,d), 7.39(2H,d), 7.56(1H, dd), 7.62(2H,d), 8.25(1H,d), 8.74(2H,m), 9.03(1H,s), 9.13 (1H,s)

Example 22

6-Methyl-2-[4-(2-methylimidazo[4,5-c]pyridin-1-yl) phenyl]-4-pentyl-1,4-dihydropyridin-3,5-dicarboxylate 3-ethylester 5-[1-methyl-3-(3-pyridyl)-2-propynyl]ester (Compound 22)

Starting material

Ethyl 4-(2-methylimidazo[4,5-c]pyridin-1-yl) benzoylacetate

3-Aminocrotonate 1-methyl-3-(3-pyridyl)-2-propynylester

Capronaldehyde

NMR: 0.84(1.5H,t), 0.89(1.5H,t), 1.02(1.5H,t), 1.03 (1.5H,t), 1.02–1.55(8H,m), 1.66(1.5H,d), 1.67(1.5H,d), 2.41 (3H,s), 2.58(3H,s), 4.01(2H,m), 4.14(0.5H,t), 4.15(0.5H,t), 5.80(1H,q), 7.09(1H,d), 7.26(1H,m), 7.40(2H,d), 7.56(2H, d), 7.74(1H,m), 8.36(1H,d), 8.54(1H,m), 8.69(1H,d), 9.06 (1H,s)

Example 23

6-Methyl-2-[4-(2-methylimidazo[4,5-c]pyridin-1-yl) phenyl]-4-(2-phenylethyl)-1,4-dihydropyridin-3,5-dicarboxylate 3-ethylester 5-[1-methyl-3-(3-pyridyl)-2-propynyl]ester (Compound 23)

Starting material

The same as in Example 22, except that 3-phenylpropanal was used as the aldehyde.

NMR: 1.01(1.5H,t), 1.02(1.5H,t), 1.67(3H,d), 1.91(2H, m), 2.43(1.5H,s), 2.44(1.5H,s), 2.58(3H,s), 2.75(2H,m), 4.01(2H,m), 4.27(0.5H,t), 4.29(0.5H,t), 5.82(0.5H,q), 5.84 (0.5H,q), 7.08(1H,d), 7.11–7.29(6H,m), 7.40(2H,d), 7.54 (2H,d), 7.63(0.5H,dt), 7.74(0.5H,dt), 8.32(1H,d), 8.53(1H, m), 8.64(0.5H,m), 8.69(0.5H,m), 9.05(1H,s)

Example 24

2-[4-(1-Imidazolyl)phenyl]-6-methyl-4-[(E)-2-phenylethenyl]-1,4-dihydropyridin-3,5-dicarboxylate 3-ethylester 5-[3-(3-pyridyl)-2-propynyl]ester (Compound 24)

520 mg of ethyl 4-(1-imidazolyl)benzoylacetate, 420 mg of 3-aminocrotonate 3-(3-pyridyl)-2-propynylester, and 300 mg of cinnamaldehyde were allowed to stand in 20 ml methanol solution containing 1 ml of acetic acid at room temperature for 1 week. The reaction solution was extracted with ethyl acetate and then the solvent was concentrated to dryness. The oily substance was purified by silica gel column chromatography to obtain the target compound in an amount of 520 mg (48.2%).

NMR: 1.02(3H,s), 2.53(3H,s), 4.81(1H,d), 5.02(2H,q), 6.32(1H,dd), 6.43(1H,d), 7.07(1H,s), 7.12(1H,s), 7.18(1H, t), 7.20(1H,t), 7.24(2H,m), 7.26(2H,d), 7.37(2H,d), 7.38 (2H,m), 7.64(1H,dt), 8.02(1H,s), 8.50(1H,dd), 8.62(1H,d)

Example 25

2-[4-(1-Imidazolyl)phenyl]-6-methyl-4-(2-phenylethyl)-1,4-dihydropyridin-3,5-dicarboxylate 3-ethylester 5-[3-(3-pyridyl)-2-propynyl]ester (Compound 25)

Starting material

Ethyl 4-(1-imidazolyl)benzoylacetate

3-Aminocrotonate 3-(3-pyridyl)2-propynylester
3-Phenylpropanal

NMR: 1.01(3H,s), 1.88(2H,m), 2.45(3H,s), 2.72(2H,m), 3.99(2H,m), 4.24(1H,t), 5.02(2H,q), 7.15(1H,t), 7.18(1H,s), 7.20–7.28(6H,m), 7.35(2H,d), 7.38(2H,d), 7.50(1H,s), 7.70 (1H,dt), 8.53(1H,dd), 8.67(1H,d)

Example 26

4-(2,2-Diphenylethyl)-2-[4-(1-imidazolyl)phenyl]-6-methyl-1 4-dihydropyridin-3,5-dicarboxylate 3-ethylester 5-[3-(3-pyridyl)-2-propynyl]ester (Compound 26)

Starting material
Ethyl 4-(1-imidazolyl)benzoylacetate
3-Aminocrotonate 3-(3-pyridyl)-2-propynylester
3,3-Diphenylpropanal NMR: 0.92(3H,s), 2.28(2H,m), 2.34(1H,m), 2.36(3H,s), 3.84(1H,m), 3.94(1H,m), 4.17(1H,t), 4.26(1H,t), 4.85(2H, q), 7.11(1H,s), 7.14(2H,m), 7.16(1s), 7.22–b 7.27(9H,m), 7.28(2H,d), 7.32(2H,d), 7.40(1H,s), 7.73(1H,dt), 8.54(1H, dd), 8.68(1H,d)

Example 27

2-[3-(1-Imidazolyl)phenyl]-6-methyl-4-(2-phenylethyl)-1,4-dihydropyridin-3,5-dicarboxylate 3-ethylester 5-[3-(3-pyridyl)-2-propynyl]ester (Compound 27)

Starting material
Ethyl 3-(1-imidazolyl)benzoylacetate
3-Aminocrotonate 3-(3-pyridyl)-2-propynylester
3-Phenylpropanal NMR: 0.96(3H,s), 1.88(2H,m), 2.42(3H,s), 2.72(2H,m), 3.96(2H,m), 4.24(1H,t), 5.02(2H,q), 7.14(1H,t), 7.15(1H,s), 7.19(1H,s), 7.17–7.25(7H,m), 7.29(1H,d), 7.40(1H,d), 7.51 (1H,t), 7.68(1H,s), 7.70(1H,s), 8.52(1H,dd), 8.65(1H,d)

Example 28

2-[3-(1-Imidazolyl)phenyl]-6-methyl-4-pentyl-1,4-dihydropyridin-3,5-dicarboxylate 3-ethylester 5-[3-(3-pyridyl)-2-propynyl]ester (Compound 28)

Starting material
The same as in Example 27, except that capronaldehyde was used as the aldehyde.

NMR: 0.85(3H,t), 0.96(3H,s), 1.28(4H,m), 1.35(2H,m), 1.49(2H,m), 2.40(3H,s), 3.95(2H,m), 4.11(1H,t), 5.01(2H, q), 7.15(1H,s), 7.23–7.31(3H,m), 7.25(1H,s), 7.42(1H,d), 7.52(1H,t), 7.75(1H,dt), 7.79(1H,s), 8.54(1H,dd), 8.69(1H, d)

Example 29

4-Cyclohexyl-2-[3-(1-imidazolyl)phenyl]-6-methyl-1,4-dihydropyridin-3,5-dicarboxylate 3-ethylester 5-[3-(3-pyridyl)-2-propynyl]ester (Compound 29)

Starting material
The same as in Example 27, except that cyclohexanecarboxaldehyde was used as the aldehyde.

NMR: 0.96(3H,s), 1.12–1.72(11H,m), 2.42(3H,s), 3.95 (2H,m), 4.09(1H,t), 5.01(2H,q), 7.15(1H,s), 7.24(1H,d), 7.25(1H,s), 7.29(1H,s), 7.32(1H,d), 7.39(1H,d), 7.55(1H,t), 7.69(1H,s), 7.73(1H,dt), 8.52(1H,dd), 8.66(1H,d)

Example 30

2-[4-(1-Imidazolyl)phenyl]-6-methyl-4-(2-phenylethyl)-1,4-dihydropyridin-3,5-dicarboxylate 3-methylester 5-[3-(3-pyridyl)-2-propynyl]ester (Compound 30)

Starting material
Methyl 4-(1-imidazolyl)benzoylacetate
3-Aminocrotonate 3-(3-pyridyl)-2-propynylester
3-Phenylpropanal NMR: 1.87(2H,m), 2.47(3H,s), 2.72(2H,m), 3.55(3H,s), 4.23(1H,t), 5.04(2H,q), 7.14(1H,t), 7.15(1H,s), 7.18–7.27 (7H,m), 7.32(2H,d), 7.33(1H,s), 7.37(2H,d), 7.71(1H,dt), 8.53(1H,dd), 8.67(1H,d)

Example 31

2-[3-(1-Imidazolyl)phenyl]-6-methyl-4-(2-phenylethyl)-1,4-dihydropyridin-3,5-dicarboxylate 3-methylester 5-[3-(3-pyridyl)-2-propynyl]ester (Compound 31)

Starting material
Methyl 3-(1-imidazolyl)benzoylacetate
3-Aminocrotonate 3-(3-pyridyl)-2-propynylester
3-Phenylpropanal NMR: 1.87(2H,m), 2.41(3H,s), 2.71(2H,m), 3.54(3H,s), 4.24(1H,t), 5.03(2H,q), 7.14(1H,t), 7.16(1H,s), 7.17–7.27 (7H,m), 7.24(1H,s), 7.30(2H,d), 7.41(1H,d), 7.53(1H,t), 7.70(1H,dt), 7.73(1H,s), 8.53(1H,dd), 8.67(1H,d)

Example 32

2-[4-(1-Imidazolyl)phenyl]-6-methyl-4-octyl-1,4-dihydropyridin-3,5-dicarboxylate 3-methylester 5-[3-(3-pyridyl)-2-propynyl]ester (Compound 32)

Starting material
Methyl 4-(1-imidazolyl)benzoylacetate
3-Aminocrotonate 3-(3-pyridyl)-2-propynylester
n-Nonylaldehyde NMR: 0.86(3H,t), 1.28(10H,m), 1.35(2H,m), 1.50(2H, m), 2.42(3H,s), 3.55(3H,s), 4.10(1H,t), 5.02(2H,q), 7.19 (1H,s), 7.26(1H,m), 7.29(1H,m), 7.29(1H,s), 7.38(2H,d), 7.41(2H,d), 7.63(1H,s), 7.75(1H,dt), 8.55(1H,dd), 8.70(1H, d)

Example 33

4-(2,2-Diphenylethyl)-2-[4-(1-imidazolyl)phenyl]-6-methyl-1,4-dihydropyridin-3,5-dicarboxylate 3-ethylester 5-[4-(3-pyridyl)-3-butynyl]ester (Compound 33)

Starting material
Ethyl 4-(1-imidazolyl)benzoylacetate
3-Aminocrotonate 4-(3-pyridyl)-3-butynylester
2,2-Diphenylpropanal NMR: 0.90(3H,s), 2.25(2H,m), 2.32(3H,s), 2.33(1H,m), 2.63(2H,m), 3.84(1H,m), 3.91(1H,m), 4.15(2H,m), 4.26 (1H,t), 4.27(1H,m), 7.13–7.28(13H,m), 7.30(2H,d), 7.34 (2H,d), 7.53(1H,s), 7.64(1H,dt), 8.49(1H,dd), 8.61(1H,d)

Example 34

6-Methyl-2-[4-(4-methylpiperazin-1-yl)phenyl]-4-(2-phenylethyl)-1,4-dihydropyridin-3,5-dicarboxylate 3-ethylester 5-[4-(3-pyridyl)-3-butynyl]ester (Compound 34)

Starting material
Ethyl 4-(4-methylpiperazin-1-yl)benzoylacetate

3-Aminocrotonate 4-(3-pyridyl)-3-butynylester
3-Phenylpropanal

NMR: 0.97(3H,s), 1.82(2H,m), 2.36(6H,s), 2.57(4H,t), 2.68(2H,t), 2.82(2H,t), 3.26(4H,t), 3.97(2H,m), 4.17(2H,m), 4.31(1H,m), 4.39(1H,m), 6.90(2H,d), 7.11–7.23(6H,m), 7.20(2H,d), 7.61(1H,dt), 8.47(1H,dd), 8.61(1H,d)

Example 35

4-(2, 2-Diphenylethyl)-2-[4-(4-methylpiperazin-1-yl)phenyl]-1,4-dihydropyridin-3,5-dicarboxylate 3-ethylester 5-[3-(3-pyridyl)-2-propynyl]ester (Compound 35)

Starting material
Ethyl 4-(4-methylpiperazin-1-yl)benzoylacetate
3-Aminocrotonate 3-(3-pyridyl)-2-propynylester
2,2-Diphenylpropanal NMR: 0.90(3H,s), 2.21(1H,m), 2.25(3H,s), 2.33(1H,m), 2.36(3H,s), 2.57(4H,t), 3.27(4H,t), 3.82(1H,m), 3.94(1H,m), 4.17(1H,t), 4.19(1H,t), 4.81(2H,q), 6.89(2H,d), 7.12(2H,m), 7.15(2H,d), 7.21–7.29(9H,m), 7.73(1H,dt), 8.54(1H,dd), 8.68(1H,d)

Example 36

4-(1,1-Difluoro-1,1a,6,10b-tetrahydrodibenzo[a,e]cyclopropa[c]cyclohepten-6-ylidenemethyl)-2-[4-(4-methylpiperazin-1-yl)phenyl]-1,4-dihydropyridin-3,5-dicarboxylate 3-ethylester 5-[3-(3-pyridyl)-2-propynyl]ester (Compound 36)

Starting material
Ethyl 4-(4-methylpiperazin-1-yl)benzoylacetate
3-Aminocrotonate 3-(3-pyridyl)-2-propenylester
1,1-Difluoro-6-formylmethyliden-1,1a,6,10b-tetrahydrodibenzo[a,e]cyclopropa[c]cycloheptene (synthesized in Reference Example 3)

NMR: 0.79(3H,s), 2.31(3H,s), 2.35(3H,s), 2.55(4H,t), 3.10(1H,t), 3.17(1H,t), 3.25(4H,t), 3.49(1H,m), 3.92(1H,m), 4.92(1H,d), 5.17(2H,q), 5.85(1H,d), 6.88(2H,d), 7.13(1H,t), 7.16–7.30(7H,m), 7.18(2H,d), 7.59(1H,dd), 7.69(1H,dt), 8.53(1H,dd), 8.67(1H,d)

Example 37

6-Methyl-2-[4-(4-methylpiperazin-1-yl)phenyl]-4-(2-phenylethyl)-1,4-dihydropyridin-3,5-dicarboxylate 3-ethylester 5-[3-(3-pyridyl)-2-propynyl]ester (Compound 37)

Starting material
Ethyl 4-(4-methylpiperazin-1-yl)benzoylacetate
3-Aminocrotonate 3-(3-pyridyl)-2-propynylester
3-Phenylpropanal NMR: 0.99(3H,s), 1.83(2H,m), 2.36(3H,s), 2.37(3H,s), 2.58(4H,t), 2.71(2H,m), 3.26(4H,t), 3.97(2H,q), 4.18(1H,t), 5.00(2H,q), 6.90(2H,d), 7.13(1H,t), 7.21–7.24(5H,m), 7.18(2H,d), 7.70(1H,dt), 8.52(1H,dd), 8.67(1H,d)

In the following Examples 38–46, since the same starting materials of Example 37 (i.e., 3-aminocrotonate 3-(3-pyridyl)-2-propynyl ester and 3-phenylpropanal) were used, except for acylacetoester, these materials were not described as the starting material.

Example 38

6-Methyl-2-[4-(4-morpholino)phenyl]-4-(2-phenylethyl )-1,4-dihydropyridin-3,5-dicarboxylate 3-ethylester 5-[3-(3-pyridyl)-2-propynyl]ester (Compound 38)

Starting material
Ethyl 4-(4-morpholino)benzoylacetate

NMR: 1.00(3H,s), 1.84(2H,m), 2.37(3H,s), 2.71(2H,m), 3.20(4H,t), 3.87(4H,t), 3.98(2H,m), 4.19(1H,t), 5.00(2H,q), 6.89(2H,d), 7.14(1H,t), 7.17–7.25(5H,m), 7.22(2H,d), 7.70(1H,dt), 8.53(1H,dd), 8.67(1H,d)

Example 39

2-[4-(1-Indolyl)phenyl]-6-methyl-4-[2-phenylethyl]-1,4-dihydropyridin-3,5-dicarboxylate 3-ethylester 5-[3-(3-pyridyl)-2-propynyl]ester (Compound 39)

Starting material
Ethyl 4-(1-indolyl)benzoylacetate

NMR: 1.00(3H,s), 1.90(2H,m), 2.41(3H,s), 2.74(2H,m), 4.00(2H,q), 4.26(1H,t), 5.02(2H,q), 6.72(1H,d), 7.15(1H,t), 7.16–7.26(7H,m), 7.36(1H,d), 7.45(2H,d), 7.56(2H,d), 7.59(1H,d), 7.71(2H,dd), 8.52(1H,dd), 8.67(1H,d)

Example 40

2-[4-(1-Indazolyl)phenyl]-6-methyl-4-(2-phenylethyl)-1,4-dihydropyridin-3,5-dicarboxylate 3-ethylester 5-[3-(3-pyridyl)-2-prolpynyl]ester (Compound 40)

Starting material
Ethyl 4-(1-indazolyl)benzoylacetate

NMR: 0.97(3H,s), 1.90(2H,m), 2.42(3H,s), 2.75(2H,m), 3.99(2H,q), 4.25(1H,t), 5.01(2H,q), 7.15(1H,s), 7.19–7.28(5H,m), 7.47(2H,d), 7.48(1H,m), 7.69(1H,dt), 7.71(1H,m), 7.80(3H,m), 7.81(2H,d), 8.23(1H,s), 8.52(1H,dd), 8.67(1H,d)

Example 41

2-[4-(1-Benzoimidazolyl)phenyl]-6-methyl-4-(2-phenylethyl)-1,4-dihydropyridin-3,5-dicarboxylate 3-ethylester 5-[3-(3-pyridyl)-2-propynyl]ester (Compound 41)

Starting material
Ethyl 4-(1-benzoimidazolyl)benzoylacetate

NMR: 1.01(3H,s), 1.90(2H,m), 2.54(3H,s), 2.76(2H,m), 4.00(2H,q), 4.28(1H,t), 5.03(2H,q), 7.15(1H,t), 7.20–7.28(5H,m), 7.46(2H,d), 7.52(1H,t), 7.59(1H,s), 7.71(1H,dt), 7.85(1H,t), 8.52(1H,dd), 8.67(1H,d)

Example 42

2-[3-(1-Benzoimidazolyl)phenyl]-6-methyl-4-(2-phenylethyl)-1,4-dihydropyridin-3,5-dicarboxylate 3-ethylester 5-[3-(3-pyridyl)-2-propynyl]ester (Compound 42)

Starting material
Ethyl 3-(1-benzoimidazolyl)benzoylacetate
3-Aminocrotonate 3-(3-pyridyl)-2-propynyl ester
3-Phenylpropanal NMR: 1.00(3H,s), 1.88(2H,m), 2.43(3H,s), 2.73(2H,m), 3.99(2H,m), 4.27(1H,t), 5.02(2H,q), 7.10(1H,t), 7.16–7.23(5H,m), 7.34(2H,m), 7.39(1H,d), 7.43(1H,s), 7.53(2H,m), 7.61(1H,t), 7.71(1H,t), 7.85(1H,dt), 7.95(1H,s), 8.52(1H,dd), 8.66(1H,d)

Example 43

2-[4-(1-Benzotriazolyl)phenyl]-6-methyl-4-(2-phenylethyl)-1,4-dihydropyridin-3,5-dicarboxylate 3-ethylester 5-[3-(3-pyridyl)-2-propynyl]ester (Compound 43)

Starting material
Ethyl 4-(1-benzotriazolyl)benzoylacetate

NMR: 1.00(3H,s), 1.90(2H,m), 2.43(3H,s), 2.74(2H,m), 4.00(2H,m), 4.27(1H,t), 5.02(2H,q), 7.15(1H,t), 7.20–7.27 (5H,m), 7.47(1H,t), 7.54(2H,d), 7.59(1H,t), 7.71(1H,dt), 7.78(1H,d), 7.85(2H,d), 8.17(1H,d), 8.53(1H,dd), 8.68(1H, d)

Example 44

6-Methyl-2-(4-methylthiophenyl)-4-(2-phenylethyl)-1,4-dihydropyridin-3,5-dicarboxylate 3-ethylester 5-[3-(3-pyridyl)-2-propynyl]ester (Compound 44)

Starting material

Ethyl 4-methylthiobenzoylacetate

NMR: 0.96(3H,s), 1.84(2H,m), 2.37(3H,s), 2.49(3H,s), 2.71(2H,m), 3.95(2H,m), 4.20(1H,t), 5.00(2H,q), 7.13(1H, t), 7.15–7.25(5H,m), 7.20(2H,d), 7.24(2H,d), 7.69(1H,dt), 8.52(1H,dd), 8.66(1H,d)

Example 45

6-Methyl-4-(2-phenylethyl)-2-[4-(3-thienyl)phenyl]-1,4-dihydropyridin-3,5-dicarboxylate 3-ethylester 5-[3-(3-pyridyl)-2-propynyl]ester (Compound 45)

Starting material

Ethyl-4-(3-thienyl)benzoylacetate

NMR: 0.95(3H,s), 1.87(2H,m), 2.39(3H,s), 2.73(2H,m), 3.98(2H,m), 4.23(1H,t), 5.01(2H,q), 7.15(1H,t), 7.18–7.24 (5H,m), 7.33(2H,d), 7.41(2H,d), 7.50(1H,t), 7.63(2H,d), 7.70(1H,dt), 8.52(1H,dd), 8.67(1H,d)

Example 46

6-Methyl-4-(2-phenylethyl)-2-[3-(3-thienyl)phenyl]-1,4-dihydropyridin-3,5-dicarboxylate 3-ethylester 5-[3-(3-pyridyl)-2-propynyl]ester (Compound 46)

Starting material

Ethyl 3-(3-thienyl)benzoylacetate

NMR: 0.88(3H,s), 1.87(2H,m), 2.39(3H,s), 2.73(2H,m), 3.92(2H,m), 4.24(1H,t), 4.99(2H,q), 7.14(1H,t), 7.19–7.47 (10H,m), 7.49(1H,s), 7.63(1H,d), 7.68(1H,dt), 8.50(1H,dd), 8.64(1H,d)

Example 47

6-Methyl-2-[4-(2-methylimidazo[4,5-c]pyridin-1-yl) phenyl]-4-(2-phenylethyl)-1,4-dihydropyridin-3,5-dicarboxylate 3-ethylester 5-[4-(3-pyridyl)-3-butynyl]ester (Compound 47)

Starting material

Ethyl 4-(2-methylimidazo[4,5-c]pyridin-1-yl) benzoylacetate

3-Aminocrotonate 4-(3-pyridyl)-2-butynylester

3-Phenylpropanal

NMR: 1.01(3H,s), 1.89(2H,m), 2.43(3H,s), 2.59(3H,s), 2.72(2H,m), 2.85(2H,t), 4.01(2H,m), 4.27(1H,t), 4.33(1H, m), 4.36(1H,m), 7.10(1H,d), 7.15–7.25(6H,m), 7.40(2H,d), 7.54(2H,d), 7.64(1H,dt), 8.35(1H,d), 8.48(1H,dd), 8.62(1H, d), 9.06(1H,s)

Example 48

4-(2,2-Diphenylethyl)-6-methyl-2-[4-(2-methylimidazo[4,5-c]pyridin-1-yl)phenyl]-1,4-dihydropyridin-3,5-dicarboxylate 3-ethylester 5-[4-(3-pyridyl)-3-butynyl]ester (Compound 48)

Starting material

The same as in Example 47 except that 3,3-diphenylpropanal was used as the aldehyde.

NMR: 0.93(3H,s), 2.28(1H,m), 2.32(3H,s), 2.38(1H,m), 2.58(3H,s), 2.64(2H,m), 3.88(1H,m), 3.95(1H,m), 4.17(2H, m), 4.27(1H,t), 4.30(1H,t), 7.09(1H,d), 7.15(2H,m), 7.20 (1H,dd), 7.25–7.27(8H,m), 7.37(2H,d), 7.45(2H,d), 7.65 (1H,dt), 8.33(1H,d), 8.49(1H,dd), 8.62(1H,d), 9.05(1H,s)

Example 49

6-Methyl-2-[3-(2-methylimidazo[4,5-c]pyridin-1-yl) phenyl]-4-(2-phenylethyl)-1,4-dihydropyridin-3,5-dicarboxylate 3-ethylester 5-[4-(3-pyridyl)-3-butynyl]ester (Compound 49)

Starting material

Ethyl 3-(2-methylimidazo[4,5-c]pyridin-1-yl) benzoylacetate

3-Aminocrotonate 4-(3-pyridyl)-3-butynylester

3-Phenylpropanal

NMR: 1.06(3H,s), 1.87(2H,m), 2.40(3H,s), 2.57(3H,s), 2.68(2H,m), 2.83(2H,t), 4.02(2H,m), 4.24(1H,t), 4.37(2H, m), 7.04(1H,t), 7.09–7.19(6H,m), 7.21(1H,s), 7.41(1H,d), 7.47(1H,d), 7.61(1H,dt), 7.65(1H,t), 8.33(1H,d), 8.46(1H, dd), 8.59(1H,d), 9.01(1H,s)

Example 50

2-[4-(2-Isopropylimidazo[4,5-c]pyridin-1-yl) phenyl]-6-methyl-4-(2-phenylethyl)-1,4-dihydropyridin-3,5-dicarboxylate 3-ethylester 5-[4-(3-pyridyl)-3-butynyl]ester (Compound 50)

Starting material

Ethyl 4-(2-isopropylimidazo[4,5-c]pyridin-1-yl) benzoylacetate

3-Aminocrotonate 4-(3-pyridyl)-3-butynylester

3-Phenylpropanal

NMR: 1.01(3H,s), 1.38(6H,d), 1.88(2H,m), 2.43(3H,s), 2.73(2H,t), 2.85(2H,t), 3.15(1H,m), 4.02(2H,m), 4.28(1H,t), 4.33(1H,m), 4.44(1H,m), 7.02(1H,d), 7.13–7.25(6H,m), 7.39(2H,d), 7.55(2H,d), 7.63(1H,dt), 8.30(1H,d), 8.48(1H, dd), 8.62(1H,d), 9.10(1H,s)

Example 51

6-Methyl-2-[4-(2-methylimidazo[4,5-b]pyridin-1-yl) phenyl]-4-(2-phenylethyl)-1,4-dihydropyridin-3,5-dicarboxylate 3-ethylester 5-[3-(3-pyridyl)-2-propynyl]ester (Compound 51)

Starting material

Ethyl 4-(2-methylimidazo[4,5-b]pyridin-1-yl) benzoylacetate

3-Aminocrotonate 3-(3-pyridyl)-2-propynylester

3-Phenylpropanal

NMR: 1.01(3H,s), 1.88(2H,m), 2.39(3H,s), 2.62(3H,S), 2.73(2H,m), 4.01(2H,q), 4.28(1H,t), 5.02(2H,q), 7.15(1H,t), 7.18–7.27(6H,m), 7.49(2H,d), 7.53(2H,d), 7.71(1H,dt), 8.03 (1H,d), 8.31(1H,dd), 8.53(1H,dd), 8.68(1H,d)

Example 52

6-Methyl-2-[4-(2-methylimidazo[4,5-b]pyridin-1-yl) phenyl]-4-pentyl-1,4-dihydropyridin-3,5-dicarboxylate 3-ethylester 5-[3-(3-pyridyl)2-propynyl]ester (Compound 52 )

Starting material

The same as in Example 51, except that capronaldehyde was used as the aldehyde.

NMR: 0.87(3H,m), 1.01(3H,s), 1.27(4H,m), 1.36(2H,m), 1.51(2H,m), 2.37(3H,s), 2.61(3H,s), 4.00(2H,m), 4.14(1H,t), 5.01(2H,q), 7.25(2H,m), 7.48(2H,d), 7.54(2H,d), 7.75(1H,dt), 8.02(1H,d), 8.30(1H,dd), 8.54(1H,dd), 8.69(1H,d)

Example 53

6-Methyl-4-[(E)-2-phenylethenyl]-2-(3-pyridyl)-1,4-dihydropyridin-3,5-dicarboxylate 3-ethylester 5-[3-(5-pyrimidyl)-2-propynyl]ester (Compound 53)

Starting material

Ethyl 2-(3-pyridylcarbonyl)acetate

3-Aminocrotonate 3-(5-pyrimidyl)-2-propynylester

Cinnamaldehyde

NMR: 0.93(3H,m), 2.44(3H,s), 3.94(2H,q), 4.82(1H,d), 5.03(2H,q), 6.30(1H,dd), 6.42(1H,d), 7.19(1H,t), 7.24–7.36 (5H,m), 7.66(1H,dt), 8.55(1H,d), 8.61(1H,dd), 8.69(2H,s), 9.11(1H,s)

Example 54

2-[4-(1-Benzimidazolyl)phenyl]-6-methyl-4-[(E)-2-phenylethenyl]-1,4-dihydropyridin-3,5-dicarboxylate 3-ethylester 5-[3-(5-pyrimidyl)-2-propynyl]ester (Compound 54)

Starting material

Ethyl 4-(1-benzimidazolyl)benzoylacetate

3-Aminocrotonate 3-(5-pyrimidyl)-2-propynylester

Cinnamaldehyde

NMR: 1.01(3H,m), 2.60(3H,s), 4.00(2H,q), 4.85(1H,d), 5.06(2H,q), 6.35(1H,dd), 6.46(1H,d), 7.20(1H,t), 7.25–7.52 (8H,m), 7.49(2H,d), 7.51(2H,d), 7.84(1H,m), 8.70(2H,s), 9.12(1H,s)

Example 55

2-[4-(1-Imidazolyl)phenyl]-6-methyl-4-(2-phenylethyl)-1,4-dihydropyridin-3,5-dicarboxylate 3-ethylester 5-[1-methyl-3-(3-pyridyl)-2-propynyl]ester (Compound 55)

Starting material

Ethyl 4-(1-imidazolyl)benzoylacetate

3-Aminocrotonate 1-methyl-3-(3-pyridyl)-2-propynylester

3-Phenylpropanal

NMR: 1.00(3H,s), 1.66(3H,d), 1.88(2H,m), 2.42(1.5H,s), 2.43(1.5H,s), 2.74(2H,m), 3.99(2H,q), 4.23(1H,t), 5.81(1H,q), 7.13(1H,t), 7.17–7.25(7H,m), 7.28(1H,s), 7.39(4H,s), 7.61(1H,s), 8.51(1H,dd), 8.63(1H,d)

Example 56

2-[3-(1-Imidazolyl)phenyl]-6-methyl-4-(2-phenylethyl)-1,4-dihydropyridin-3,5-dicarboxylate 3-methylester 5-[1-methyl-3-(3-pyridyl)-2-propynyl]ester (Compound 56)

Starting material

Methyl 3-(1-imidazolyl)benzoylacetate

3-Aminocrotonate 1-methyl-3-(3-pyridyl)-2-propynylester

3-Phenylpropanal

NMR: 1.66(3H,d), 1.87(2H,m), 2.40(1.5H,s), 2.41(1.5H,s), 2.72(2H,m), 3,53(3H,s), 4.22(1H,t), 5.82(1H,q), 7.13(1H,t), 7.14–7.28(4H,m), 7.15(2H,d), 7.18(2H,d), 7.30(1H,d), 7.41(1H,d), 7.52(1H,t), 7.62(1H,dt), 7.73(1H,s), 8.50(1H,dd), 8.62(1H,d)

Example 57

6-Methyl-2-[3-(2-methylimidazo[4,5-c]pyridin-1-yl)phenyl]-4-[2-phenylethyl]-1,4-dihydropyridin-3,5-dicarboxylate 3-ethylester 5-[1-methyl-3-(3-pyridyl)-2-propynyl]ester (Compound 57)

Starting material

Ethyl 3-(2-methylimidazo[4,5-c]pyridin-1-yl) benzoylacetate

3-Aminocrotonate 1-methyl-3-(3-pyridyl)-2-propynylester

3-Phenylpropanal

NMR: 1.08(3H,s), 1.65(3H,d), 1.87(2H,m), 2.40(3H,s), 2.58(3H,s), 2.72(2H,m), 4.05(2H,m), 4.24(0.5H,t), 4.25(0.5H,t), 5.80(1H,m), 7.06(1H,t), 7.12–7.23(5H,m), 7.14(1H,s), 7.42(2H,d), 7.48(1H,d), 7.65(2H,q), 7.73(1H,dt), 8.36(1H,d), 8.52(1H,dd), 8.65(1H,d), 9.03(1H,s)

Example 58

4-(2,2-Diphenylethyl)-6-methyl-2-[4-(2-methylimidazo[4,5-c]pyridin-1-yl)phenyl]-1,4-dihydropyridin-3,5-dicarboxylate 3-methylester 5-[1-methyl-3-(3-pyridyl)-2-propynyl]ester (Compound 58)

Starting material

Ethyl 4-(2-methylimidazo[4,5-c]pyridin-1-yl) benzoylacetate

3-Aminocrotonate 1-methyl-3-(3-pyridyl)-2-propynylester 3,3-Diphenylpropanal

NMR: 0.90(3H,s), 1.56(3H,m), 2.31(1.5H,s), 2.33(1.5H,s), 2.35(2H,m), 2.58(3H,s), 3.83(1H,m), 3.97(1H,m), 4.22(1H,m), 4.33(1H,m), 5.68(0.5H,q), 5.76(0.5H,q), 7.08(1H,d), 7.11–7.33(11H,m), 7.36(2H,d), 7.44(2H,d), 7.72(1H,m), 8.29(1H,d), 8.53(1H,m), 8.67(0.5H,d), 8.70(0.5H,d), 9.03(1H,s)

Example 59

4-(3-Cyclohexylpropyl)-6-methyl-2-[4-(2-methylimidazo[4,5-c]pyridin-1-yl)phenyl]-1,4-dihydropyridin-3,5-dicarboxylate 3-ethylester 5-[3-(3-pyridyl)-2-propynyl]ester (Compound 59)

Starting material

Ethyl 4-(2-methylimidazo[4,5-c]pyridin-1-yl) benzoylacetate

3-Aminocrotonate 3-(3-pyridyl)-2-propynylester

4-Cyclohexylbutanal

NMR: 0.85(3H,m), 1.04(3H,s), 1.18(6H,m), 1.36(2H,m), 1.49(2H,m), 1.66(5H,m), 2.42(3H,s), 2.59(3H,s), 4.01(2H,m), 4.14(1H,t), 5.03(2H,q), 7.11(1H,d), 7.27(1H,dd), 7.42(2H,d), 7.56(1H,dt), 7.57(2H,d), 8.38(1H,d), 8.55(1H,dd), 9.06(1H,s)

In the following Examples 60–69, since the same starting materials of Example 59 (i.e., ethyl 4-(2-methylimidazo[4,5-c]pyridin-1-yl)benzoylacetate and 3-aminocrotonate 3-(3-pyridyl)-2-propynylester), except for the aldehyde, were used, these materials were not described as the starting material.

Example 60

4-(2,2-Diphenylethyl)-6-methyl-2-[4-(2-methylimidazo[4 5-c]pyridin-1-yl)phenyl]-1,4-dihydropyridin-3,5-dicarboxylate 3-ethylester 5-[3-(3-pyridyl)-2-propynyl]ester (Compound 60)

Starting material
3,3-Diphenylpropanal

NMR: 0.95(3H,s), 2.30(1H,m), 2.31(1H,m), 2.34(3H,s), 2.59(3H,s), 3.89(1H,m), 3.99(1H,m), 4.19(1H,t), 4.30(1H,t), 4.85(2H,q), 7.10(1H,d), 7.15(2H,m), 7.23–7.31(9H,m), 7.38(2H,d), 7.44(2H,d), 7.73(1H,dt), 8.36(1H,d), 8.56(1H,dd), 8.69(1H,d), 9.06(1H,s)

Example 61

4-(2,2-Diphenylethenyl)-6-methyl-2-[4-(2-methylimidazo[4,5-c]pyridin-1-yl)phenyl]-1,4-dihydropyridin-3,5-dicarboxylate 3-ethylester 5-[3-(3-pyridyl)-2-propynyl]ester (Compound 61)

Starting material
3,3-Diphenyl-2-propenal

NMR: 0.94(3H,s), 2.41(3H,s), 2.59(3H,s), 3.84(1H,m), 3.99(1H,m), 4.69(2H,q), 5.01(2H,d), 6.07(1H,d), 7.09(1H,d), 7.22–7.25(6H,m), 7.32(1H,t), 7.39(2H,d), 7.41(2H,m), 7.48(2H,d), 7.59(2H,d), 7.69(1H,dt), 8.34(1H,dd), 8.53(1H,dd), 8.65(1H,d), 9.06(1H,s)

Example 62

4-[2-(3-Cyclopentylmethyloxy-4-methoxyphenyl)ethyl]-6-methyl-2-[4-(2-methylimidazo[4,5-c]pyridin-1-yl)phenyl]-1,4-dihydropyridin-3,5-dicarboxylate 3-ethylester 5-[3-(3-pyridyl)-2-propynyl]ester (Compound 62)

Starting material
3-(3-Cyclopentylmethyloxy-4-methoxyphenyl)propanal

NMR: 1.03(3H,s), 1.33(2H,m), 1.60(4H,m), 1.84(4H,m), 2.42(1H,m), 2.46(3H,s), 2.58(3H,s), 2.67(2H,m), 3.82(3H,s), 3.84(2H,d), 4.02(2H,m), 4.28(1H,t), 5.04(2H,q), 6.74(1H,s), 6.75(2H,q), 7.08(1H,d), 7.23(1H,dd), 7.40(2H,d), 7.55(2H,d), 7.70(1H,dt), 8.32(1H,d), 8.54(1H,dd), 8.68(1H,d), 9.05(1H,s)

Example 63

4-[2-[3-[2-(4-Fluorophenyl)ethyloxy]-4-methoxyphenyl]ethyl]-6-methyl-2-[4-(2-methylimidazo[4 ,5-c]pyridin-1-yl)phenyl]-1,4-dihydropyridin-3,5-dicarboxylate 3-ethylester 5-[3-(3-pyridyl)-2-propynyl]ester (Compound 63)

Starting material
3-[3-[2-(4-Fluorophenyl)ethyloxyl-4-methoxyphenyl]propanal

NMR: 1.00(3H,s), 1.83(2H,m), 2.45(3H,s), 2.58(3H,s), 2.66(2H,m), 3.10(2H,t), 3.82(3H,s), 4.00(2H,m), 4.15(2H,t), 4.26(1H,t), 5.02(2H,q), 6.70(1H,s), 6.76(2H,q), 6.98(2H,t), 7.07(1H,d), 7.20–7.25(3H,m), 7.38(2H,d), 7.54(2H,d), 7.69(1H,dt), 8.30(1H,d), 8.53(1H,dd), 8.67(1H,d), 9.04(1H,s)

Example 64

4-[2-[4-Methoxy-3-[2-(4-methylthiazole-5-yl)ethyloxy]phenyl]ethyl]-6-methyl-2-[4-(2-methylimidazo[4,5-c]pyridin-1-yl)phenyl]-1,4-dihydropyridin-3,5-dicarboxylate 3-ethylester 5-[3-(3-pyridyl)-2-propynyl]ester (Compound 64)

Starting material
3-[4-Methoxy-3-[2-(4-methylthiazol-5-yl)ethyloxy]phenyl]propanal NMR: 1.01(3H,s), 1.86(2H,m), 2.44(3H,s), 2.46(3H,s), 2.57(3H,s), 2.67(2H,m), 3.28(2H,t), 3.83(3H,s), 4.00(2H,m), 4.14(2H,t), 4.27(1H,t), 5.03(2H,q), 6.71(1H,s), 6.78(2H,s), 7.05(1H,d), 7.22(1H,dd), 7.37(2H,d), 7.54(2H,d), 7.69(1H,dt), 8.27(1H,d), 8.53(1H,dd), 8.67(1H,d), 9.03(1H,s)

Example 65

4-(2-Indanylmethyl)-6-methyl-2-[4-(2-methylimidazo[4,5-c]pyridin-1-yl)phenyl]-1,4-dihydropyridin-3,5-dicarboxylate 3-ethylester 5-[3-(3-pyridyl)-2-propynyl]ester (Compound 65)

Starting material
2-Indanyl acetaldehyde

NMR: 1.04(3H,s), 1.73(2H,t), 2.46(3H,s), 2.58(3H,s), 2.66(1H,m), 3.20(2H,m), 4.01(2H,m), 4.23(1H,t), 5.04(2H,q), 7.09(4H,m), 7.14(1H,m), 7.19(1H,dd), 7.39(2H,d), 7.56(1H,m), 7.57(2H,d), 8.31(1H,d), 8.52(1H,dd), 8.61(1H,d), 9.05(1H,s)

Example 66

4-(1,1-Difluoro-1,1a,6, 10b-tetrahydrodibenzoa,[a,e]cyclopropa[c]cyclohepten-6-ylmethyl)-6-methyl-2-[4-(2-methylimidazo[4,5-c]pyridin-1-yl)phenyl]-1,4-dihydropyridin-3,5-dicarboxylate 3-ethylester 5-[3-(3-pyridyl)-2-propynyl]ester (Compound 66)

Starting material
1,1-Difluoro-6-formylmethyl-1,1a,6,10b-tetrahydrodibenzo[a,e]cyclopropa[c]cycloheptene (synthesized in Reference Example 4)

NMR: 0.94(3H,s), 2.33(3H,s), 2.54(1H,m), 2.57(3H,s), 2.76(1H,m), 3.27(2H,d), 3.99(1H,m), 4.30(1H,t), 4.93(2H,q), 5.85(1H,d), 6.88(2H,d), 7.32(4H,s), 7.73(1H,dt), 8.25(1H,d), 8.56(1H,dd), 8.68(1H,d), 9.02(1H,s)

Example 67

4-(1,1-Difluoro-1,1a,6,10b-tetrahydrodibenzo[a,e]cyclopropa[c]cyclohepten-6-ylidenemethyl)-6-methyl-2-[4-(2-methylimidazo[4,5-c]pyridin-1-yl)phenyl]-1,4-dihydropyridin-3,5-dicarboxylate 3-ethylester 5-[3-(3-pyridyl)-2-propynyl]ester (Compound 67)

Starting material
1,1-Difluoro-6-formylmethyliden-1,1a,6,10b-tetrahydrodibenzo[a,e]cyclopropa[c]cycloheptene NMR: 0.83(3H,s), 2.39(3H,s), 2.57(3H,s), 3.14(2H,m), 3,58(1H,m), 3.96(1H,m), 5.01(1H,d), 5.15(2H,q), 5.90(1H,d), 7.07(1H,d), 7.37(2H,d), 7.54(2H,d), 7.62(1H,d), 7.71(1H,dt), 8.28(1H,d), 8.55(1H,dd), 8.69(1H,d), 9.03(1H,s)

Example 68

4-[2-(3,4-Dimethoxyphenyl)propyl]-6-methyl-2-[4-(2-methylimidazo[4,5-c]pyridin-1-yl)phenyl]-1,4-dihydropyridin-3,5-dicarboxylate 3-ethylester 5-[3-(3-pyridyl)-2-propynyl]ester (Compound 68)

Starting material
3-(3,4-Dimethoxyphenyl)butanal

NMR: 1.00(1.5H,s), 1.04(1.5H,s), 1.32(1.5H,s), 1.35(1.5H,s), 1.71(2H,m), 2.35(1.5H,s), 2.43(1.5H,s), 2.58(1.5H,s), 2.59(1.5H,s), 2.85(1H,m), 3.82(1.5H,s), 3.83(1.5H,s), 3.85(1.5H,s), 3.88(1.5H,s), 4.01(2H,m), 4.23

(0.5H,t), 4.25(0.5H,t), 4.96(1H,q), 5.12(1H,q), 6.73(1H,s), 6.77(1H,s), 6.79(1H,s), 7.09(1H,t), 7.25(1H,m), 7.38(1H,d), 7.74(1H,m), 8.36(0.5H,d), 8.37(0.5H,d), 8.55(1H,dd), 8.70(1H,m), 9.06(1H,s)

Example 69

4-[2-(3,4-Dimethoxyphenyl-1-propenyl)]-6-methyl-2-[4-(2-methylimidazo[4,5-c]pyridin-1-yl)phenyl]-1,4-dihydropyridin-3,5-dicarboxylate 3-ethylester 5-[3-(3-pyridyl)-2-propynyl]ester (Compound 69)

Starting material 3-(3,4-Dimethoxyphenyl)-2-butenal

NMR: 1.06(3H,s), 2.35(3H,s), 2.45(3H,s), 2.58(3H,s), 3.87(6H,s), 4.01(2H,m), 5.01(2H,q), 5.07(1H,d), 6.79(1H,d), 6.94(1H,d), 6.98(1H,dd), 7.08(1H,d), 7.23(1H,dd), 7.39(2H,d), 7.59(2H,d), 7.65(1H,dt), 8.30(1H,d), 8.54(1H,dd), 8.66(1H,m), 9.04(1H,s)

Example 70

2-[4-(2-Isopropylimidazo[4,5-c]pyridin-1-yl)phenyl]-6-methyl-4-(2-phenylethyl)-1,4-dihydropyridin-3,5-dicarboxylate 3-ethylester 5-[3-(3-pyridyl)-2-propynyl]ester (Compound 70)

Starting material

Ethyl 4-(2-isopropylimidazo[4,5-c]pyridin-1-yl)benzoylacetate

3-Aminocrotonate 3-(3-pyridyl)-2-propynylester

3-Phenylpropanal

NMR: 1.03(3H,s), 1.37(3H,d), 1.39(3H,d), 1.91(2H,m), 2.45(3H,s), 2.75(2H,m), 3.16(1H,m), 4.03(2H,m), 4.29(1H,t), 5.04(2H,q), 7.01(1H,d), 7.14–7.25(6H,m), 7.39(2H,d), 7.55(2H,d), 7.72(1H,dt), 8.26(1H,d), 8.54(1H,dd), 8.68(1H,d), 9.09(1H,s)

Example 71

4-(2,2-Diphenylethyl)-2-[4-(2-isopropylimidazo[4,5-c]pyridin-1-yl)phenyl]-6-methyl-1,4-dihydropyridin-3,5-dicarboxylate 3-ethylester 5-[3-(3-pyridyl)-2-propynyl]ester (Compound 71)

Starting material

The same as in Example 70, except that 3,3-diphenylpropanal was used as the aldehyde.

NMR: 0.95(3H,s), 1.37(3H,d), 1.38(3H,d), 2.30(2H,m), 2.36(3H,s), 3.15(1H,m), 3.89(1H,m), 3.99(1H,m), 4.19(1H,t), 4.31(1H,t), 4.86(2H,q), 7.00(1H,d), 7.15(2H,m), 7.23–7.32(9H,m), 7.34(2H,d), 7.44(2H,d), 7.74(1H,dt), 8.21(1H,d), 8.55(1H,dd), 8.69(1H,d), 9.08(1H,s)

Example 72

4-(2,2-Diphenylethyl)-6-methyl-2-[3-(2-methylimidazo[4,5-c]pyridin-1-yl)phenyl]-1,4-dihydropyridin-3,5-dicarboxylate 3-ethylester 5-[3-(3-pyridyl)-2-propynyl]ester (Compound 72)

Starting material

Ethyl 3-(2-methylimidazo[4,5-c]pyridin-1-yl)benzoylacetate

3-Aminocrotonate 3-(3-pyridyl)-2-propynyl ester 3,3-Diphenylpropanal

NMR: 1.06(3H,t), 2.32(2H,t), 2.35(3H,s), 2.56(3H,s), 3.98(2H,q), 4.14(1H,t), 4.28(1H,t), 4.86(2H,q), 6.89(1H,s), 6.96(2H,m), 7.10–7.25(10H,m), 7.39(2H,d), 7.63(1H,t), 7.70(1H,dt), 8.37(1H,d), 8.54(1H,dd), 8.67(1H,d), 9.05(1H,s)

Example 73

6-Methyl-2-[3-(2-methylimidazo[4,5-c]pyridin-1-yl)phenyl]-4-(2-phenylethyl-1,4-dihydropyridin-3,5-dicarboxylate 3-ethylester 5-[3-(3-pyridyl)-2-propynyl]ester (Compound 73)

Starting material

Ethyl 3-(2-methylimidazo[4,5-c]pyridin-1-yl)benzoylacetate

3-Aminocrotonate 3-(3-pyridyl)-2-propynylester

3-Phenylpropanal

NMR: 1.09(3H,s), 1.89(2H,m), 2.41(3H,s), 2.58(3H,S), 2.71(2H,m), 4.02(1H,m), 4.08(1H,m), 4.24(1H,t), 5.02(2H,q), 7.05(1H,t), 7.13–7.24(7H,m), 7.42(1H,d), 7.48(1H,d), 7.67(1H,t), 7.70(1H,dt), 8.38(1H,d), 8.54(1H,dd), 8.67(1H,d), 9.05(1H,s)

Example 74

6-Methyl-4-(2-phenylethyl)-2-[3-(2-trifluoromethylimidazo[4,5-c]pyridin-1-yl)phenyl]-1,4-dihydropyridine-3,5-dicarboxylate 3-ethylester 5-[3-(3-pyridyl)-2-propinyl]ester (Compound 74)

Starting material

Ethyl 3-(2-trifluoromethylimidazo[4,5-c]pyridin-1-yl)benzoylacetate

3-Aminocrotonate 3-(3-pyridyl)-2-propynylester

3-Phenylpropanal

NMR: 1.10(3H,s), 1.87(2H,m), 2.41(3H,s), 2.70(2H,m), 4.03(1H,m), 4.09(1H,m), 4.24(1H,t), 5.02(2H,q), 7.02(1H,m), 7.14(2H,s), 7.21(1H,s), 7.23(1H,dd), 7.24(3m,d), 7.50(1H,d), 7.54(1H,d), 7.66(1H,t), 7.68(1H,dt), 8.53(1H,dd), 8.56(1H,dd), 8.67(1H,d), 9.30(1H,s)

Example 75

6-Methyl-2-[4-(2-methylimidazo[4,5-c]pyridin-1-yl)phenyl]-4-[2-(3-trifluoromethylphenyl)ethyl]-1,4-dihydropyridin-3,5-dicarboxylate 3-ethylester 5-[3-(3-pyridyl)-2-propynyl]ester (Compound 75)

Starting material

Ethyl 4-(2-methylimidazo[4,5-c]pyridin-1-yl)benzoylacetate

3-Aminocrotonate 3-(3-pyridyl)-2-propynylester 3-(3-Trifluoromethylphenyl)propanal NMR: 1.01(3H,s), 1.90(2H,m), 2.45(3H,s), 2.58(3H,s), 2.81(2H,m), 4.02(2H,q), 4.29(1H,t), 5.04(2H,q), 7.08(1H,d), 7.23(1H,m), 7.35–7.45(4H,m), 7.41(2H,d), 7.53(2H,d), 7.71(1H,dt), 8.32(1H,d), 8.54(1H,dd), 8.68(1H,d), 9.05(1H,s)

In the following Examples 76–80, since the same starting materials of Example 75, except for the aldehyde, (i.e., ethyl 4-(2-methylimidazo[4,5-c]pyridin-1-yl)benzoylacetate and 3-aminocrotonate 3-(3-pyridyl)-2-propynylester), these materials were not described as the starting materials.

Example 76

4-[2-(4-Isopropylphenyl)ethyl]-6-methyl-2-[4-(2-methylimidazor[4,5-c]pyridin-1-yl)phenyl1-1,4-dihydropyridin-3,5-dicarboxylate 3-ethylester 5-[3-(3-pyridyl)-2-propynyl]ester (Compound 76)

Starting material 3-(4-Isopropylphenyl)propanal

NMR: 1.03(3H,s), 1.22(6H,d), 1.90(2H,m), 2.45(3H,s), 2.58(3H,s), 2.73(2H,m), 2.86(1H,m), 4.02(2H,q), 4.28(1H,t), 5.03(2H,q), 7.07(1H,d), 7.11(2H,d), 7.13(2H,d), 7.23(1H,dd), 7.38(2H,d), 7.54(2H,d), 7.73(1H,dt), 8.28(1H,d), 8.54(1H,dd), 8.70(1H,d), 9.04(1H,S)

Example 77

6-Methyl-2-[4-(2-methylimidazo[4,5c-]pyridin-1-yl)phenyl]-4-[2-naphthyl)ethyl]-1,4-dihydropyridin-3,5-dicarboxylate 3-ethylester -5-[3-(3-pyridyl)-2-propynyl]ester (Compound 77)

Starting material 3-(2-naphthyl)propanal

NMR: 1.01(3H,s), 2.00(2H,m), 2.47(3H,s), 2.57(3H,s), 2.92(2H,m), 4.02(2H,m), 4.34(1H,t), 5.05(2H,q), 7.05(1H,d), 7.17(1H,dd), 7.33(1H,m), 7.34(2H,d), 7.41(2H,m), 7.49(2H,d), 7.64(1H,s), 7.68(1H,dt), 7.73(2H,d), 7.78(1H,dd), 8.28(1H,d), 8.51(1H,dd), 8.69(1H,d), 9.04(1H,s)

Example 78

4-]2,2-Bis(4-fluorophenyl)ethyl]-6-methyl-2-[4-(2-methylimidazo[4,5-c]pyridin-1-yl )phenyl]-1,4-dihydropyridin-3,5-dicarboxylate 3-ethylester 5-[3-(3-pyridyl])-2-propynyl]ester (Compound 78)

Starting material 3,3-Bis(4-fluorophenyl)propanal

NMR: 0.94(3H,s), 2.22(1H,m), 2.30(1H,m), 2.38(3H,s), 2.58(3H,s), 3.90(1H,m), 3.97(1H,m), 4.15(1H,t), 4.24(1H,t), 4.87(2H,q), 6.96(4H,q), 7.08(1H,d), 7.19–7.29(5H,m), 7.39(2H,d), 7.48(2H,d), 7.74(1H,dt), 8.32(1H,d), 8.56(1H,dd), 8.69(1H,d), 9.05(1H,s)

Example 79

6-Methyl-2-[4-(2-methylimidazo[5-c]pyridin-1-yl)phenyl]-4-(3-phenylprolpyl)-1,4-dihydropyridin-3,5-dicarboxylate 3-ethylester 5-[3-(3-pyridyl)-2-propynyl]ester (Compound 79)

Starting material

4-Phenylbutanal

NMR: 1.01(3H,s), 1.61(2H,m), 1.74(2H,m), 2.42(3H,s), 2.58(3H,s), 2.65(2H,m), 4.01(2H,m), 4.20(1H,t), 5.02(2H,q), 7.08(1H,d), 7.15(1H,t), 7.18–7.25(5H,m), 7.39(2H,d), 7.53(2H,d), 7.72(1H,dt), 8.33(1H,d), 8.55(1H,dd), 8.68(1H,d), 9.05(1H,s)

Example 80

6-Methyl-2-[4-(2-methylimidazo[4,5-c]pyridin-1-yl)phenyl]-4-(5-phenylpentyl )-1,4-dihydropyridin-3,5-dicarboxylate 3-ethylester 5-[3-(3-pyridyl)-2-propynyl]ester (Compound 80)

Starting material

6-Phenylhexanal

NMR: 1.03(3H,s), 1.39(4H,m), 1.53(2H,m), 1.61(2H,m), 2.43(3H,s), 2.57(2H,m), 2.58(3H,s), 4.01(2H,m), 4.15(1H,t), 5.02(2H,q), 7.07(1H,d), 7.14–7.27(6H,m), 7.38(2H,d), 7.55(2H,d), 7.73(1H,dt), 8.30(1H,d), 8.54(1H,dd), 8.69(1H,d), 9.04(1H,s)

The structures of the substituents of the compounds (Compound 1 to Compound 80) obtained in the above Examples are shown in Table 1 to Table 11.

TABLE 1

| Compound | $R_1$ | $R_2$ | $R_3$ | $R_4$ |
|---|---|---|---|---|
| Compound 1 | 4-(2-methylimidazo[4,5-c]pyridin-1-yl)phenyl | ethyl | —CH$_3$ | 2-chlorophenylpropyl |
| Compound 2 | 4-(2-methylimidazo[4,5-c]pyridin-1-yl)phenyl | ethyl | 2,2-dimethylbutyl | 3-(3-pyridyl)-2-propynyl |

TABLE 1-continued

| Compound | R₁ | R₂ | R₃ | R₄ |
|---|---|---|---|---|
| Compound 3 | 4-(2-methyl-1H-imidazo[4,5-c]pyridin-1-yl)phenyl | propyl (CH₂CH₂CH₃) | hexyl | 4-(pyridin-3-yl)but-3-yn-1-yl |
| Compound 4 | 4-(2-methyl-1H-imidazo[4,5-c]pyridin-1-yl)phenyl | propyl | cyclohexyl | 4-(pyridin-3-yl)but-3-yn-1-yl |
| Compound 5 | 4-(2-methyl-1H-imidazo[4,5-c]pyridin-1-yl)phenyl | propyl | 3-(methylthio)propyl (CH₂CH₂CH₂SCH₃) | 4-(pyridin-3-yl)but-3-yn-1-yl |
| Compound 6 | 4-(2-methyl-1H-imidazo[4,5-c]pyridin-1-yl)phenyl | propyl | benzyl | 4-(pyridin-3-yl)but-3-yn-1-yl |
| Compound 7 | 4-(2-methyl-1H-imidazo[4,5-c]pyridin-1-yl)phenyl | propyl | 2-phenylpropyl (isopropylbenzene-linked) | 4-(pyridin-3-yl)but-3-yn-1-yl |

TABLE 2

| Compound | R₁ | R₂ | R₃ | R₄ |
| --- | --- | --- | --- | --- |
| Compound 8 | 1-(4-methylphenyl)-2-methyl-imidazo[4,5-c]pyridine | CH₃ | propenyl-cyclohexyl | 3-(prop-2-ynyl)pyridine |
| Compound 9 | 1-(4-methylphenyl)-2-methyl-imidazo[4,5-c]pyridine | CH₃ | propylphenyl | 3-(prop-2-ynyl)pyridine |
| Compound 10 | 1-(4-methylphenyl)-2-methyl-imidazo[4,5-c]pyridine | CH₃ | propenylphenyl | 3-(prop-2-ynyl)pyridine |
| Compound 11 | 1-(4-methylphenyl)-2-methyl-imidazo[4,5-c]pyridine | CH₃ | 2-chloro-propylphenyl | 3-(prop-2-ynyl)pyridine |
| Compound 12 | 1-(4-methylphenyl)-2-methyl-imidazo[4,5-c]pyridine | CH₃ | 2-chloro-propenylphenyl | 3-(prop-2-ynyl)pyridine |
| Compound 13 | 1-(4-methylphenyl)-2-methyl-imidazo[4,5-c]pyridine | CH₃ | 2-methoxy-propylphenyl | 3-(prop-2-ynyl)pyridine |

TABLE 2-continued

| Compound | R₁ | R₂ | R₃ | R₄ |
|---|---|---|---|---|
| Compound 14 | 1-(4-methylphenyl)-2-methyl-1H-imidazo[4,5-c]pyridine | propyl | 2-methoxy-(1-propenyl)phenyl | 3-(but-2-ynyl)pyridine |

TABLE 3

| Compound | R₁ | R₂ | R₃ | R₄ |
|---|---|---|---|---|
| Compound 15 | 1-(4-methylphenyl)-2-methyl-1H-imidazo[4,5-c]pyridine | propyl | 2-propylfuran | 3-(but-2-ynyl)pyridine |
| Compound 16 | 1-(4-methylphenyl)-2-methyl-1H-imidazo[4,5-c]pyridine | propyl | 2-(1-propenyl)furan | 3-(but-2-ynyl)pyridine |
| Compound 17 | 1-(4-methylphenyl)-2-methyl-1H-imidazo[4,5-c]pyridine | propyl | 3-propylthiophene | 3-(but-2-ynyl)pyridine |
| Compound 18 | 1-(4-methylphenyl)-2-methyl-1H-imidazo[4,5-c]pyridine | propyl | propylbenzene | 3-(but-2-ynyl)quinoline |

TABLE 3-continued

| Compound | R₁ | R₂ | R₃ | R₄ |
| --- | --- | --- | --- | --- |
| Compound 19 | 1-(4-methylphenyl)-2-methyl-imidazo[4,5-c]pyridine | CH₃CH₂- | (E)-2-phenylpropenyl | 3-(quinolin-3-yl)prop-2-ynyl |
| Compound 20 | 1-(4-methylphenyl)-2-methyl-imidazo[4,5-c]pyridine | CH₃CH₂- | (E)-2-phenylpropenyl | 3-(isoquinolin-4-yl)prop-2-ynyl |
| Compound 21 | 1-(4-methylphenyl)-2-methyl-imidazo[4,5-c]pyridine | CH₃CH₂- | (E)-1-(2-chlorophenyl)propenyl | 3-(pyrimidin-5-yl)prop-2-ynyl |

TABLE 4

| Compound | R₁ | R₂ | R₃ | R₄ |
| --- | --- | --- | --- | --- |
| Compound 22 | 1-(4-methylphenyl)-2-methyl-imidazo[4,5-c]pyridine | CH₃CH₂- | n-pentyl | 3-methyl-4-(pyridin-3-yl)but-3-yn-2-yl |
| Compound 23 | 1-(4-methylphenyl)-2-methyl-imidazo[4,5-c]pyridine | CH₃CH₂- | 3-phenylpropyl | 3-methyl-4-(pyridin-3-yl)but-3-yn-2-yl |

TABLE 4-continued
| Compound | R₁ | R₂ | R₃ | R₄ |
|---|---|---|---|---|
| Compound 24 | 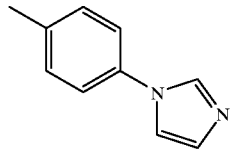 | 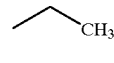 | 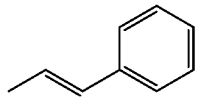 | 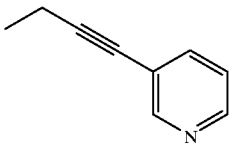 |
TABLE 5
| Compound | R₁ | R₂ | R₃ | R₄ |
|---|---|---|---|---|
| Compound 25 | 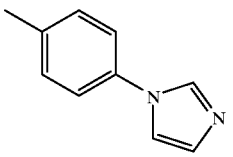 | 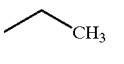 | 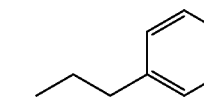 | 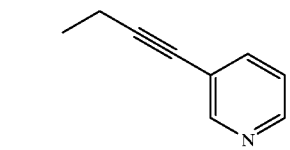 |
| Compound 26 | 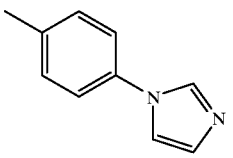 | 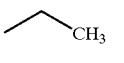 | 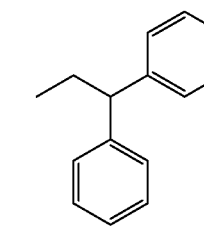 | 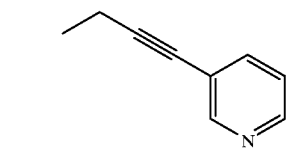 |
| Compound 27 | 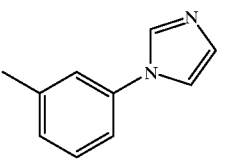 | 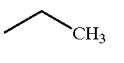 | 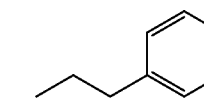 | 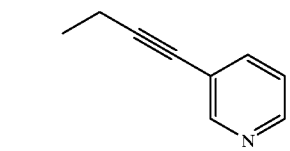 |
| Compound 28 | 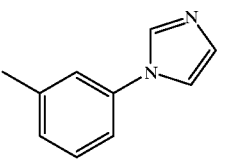 | 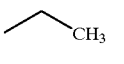 | 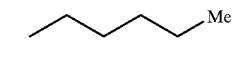 | 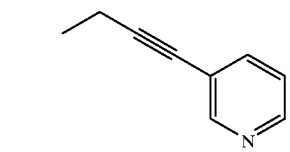 |
| Compound 29 | 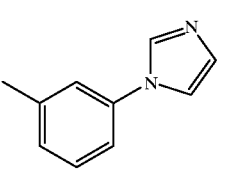 | 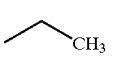 | 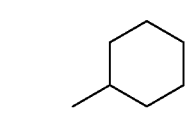 | 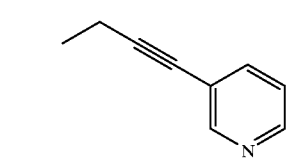 |
| Compound 30 | 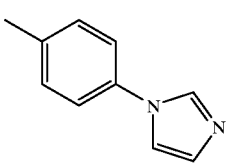 | CH₃ |  | 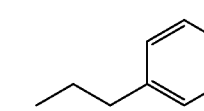 |

TABLE 5-continued

| Compound | R₁ | R₂ | R₃ | R₄ |
|---|---|---|---|---|
| Compound 31 | 3-(imidazol-1-yl)methylphenyl | CH₃ | 3-phenylpropyl | 3-(pyridin-3-yl)prop-2-ynyl |
| Compound 32 | 4-(imidazol-1-yl)methylphenyl | CH₃ | n-nonyl | 3-(pyridin-3-yl)prop-2-ynyl |

TABLE 6

| Compound | R₁ | R₂ | R₃ | R₄ |
|---|---|---|---|---|
| Compound 33 | 4-(imidazol-1-yl)methylphenyl | ethyl-CH₃ | 1,1-diphenylpropyl | 4-(pyridin-3-yl)but-3-ynyl |
| Compound 34 | 4-(4-methylpiperazin-1-yl)methylphenyl | ethyl-CH₃ | 3-phenylpropyl | 4-(pyridin-3-yl)but-3-ynyl |
| Compound 35 | 4-(4-methylpiperazin-1-yl)methylphenyl | ethyl-CH₃ | 1,1-diphenylpropyl | 4-(pyridin-3-yl)but-3-ynyl |
| Compound 36 | 4-(4-methylpiperazin-1-yl)methylphenyl | ethyl-CH₃ | 11,11-difluoro-5H-dibenzo[a,d]cycloheptene-5-ylidene derivative | 4-(pyridin-3-yl)but-3-ynyl |

TABLE 6-continued

| Compound | R₁ | R₂ | R₃ | R₄ |
| --- | --- | --- | --- | --- |
| Compound 37 | 4-(4-methylphenyl)-1-methylpiperazine | CH₃ (ethyl) | propylphenyl | 3-pyridyl-ethynyl-ethyl |
| Compound 38 | 4-(4-methylphenyl)morpholine | CH₃ (ethyl) | propylphenyl | 3-pyridyl-ethynyl-ethyl |
| Compound 39 | 1-(4-methylphenyl)-1H-indole | CH₃ (ethyl) | propylphenyl | 3-pyridyl-ethynyl-ethyl |
| Compound 40 | 1-(4-methylphenyl)-1H-indazole | CH₃ (ethyl) | propylphenyl | 3-pyridyl-ethynyl-ethyl |

TABLE 7

| Compound | R₁ | R₂ | R₃ | R₄ |
| --- | --- | --- | --- | --- |
| Compound 41 | 1-(4-methylphenyl)-1H-benzimidazole | CH₃ (ethyl) | propylphenyl | 3-pyridyl-ethynyl-ethyl |
| Compound 42 | 1-(3-methylphenyl)-1H-benzimidazole | CH₃ (ethyl) | propylphenyl | 3-pyridyl-ethynyl-ethyl |

TABLE 7-continued

| Compound | R₁ | R₂ | R₃ | R₄ |
|---|---|---|---|---|
| Compound 43 | 1-(p-tolyl)-1H-benzotriazole | CH₃CH₂– | propylphenyl | 3-(but-1-yn-1-yl)pyridine |
| Compound 44 | 4-(methylthio)toluene | CH₃CH₂– | propylphenyl | 3-(but-1-yn-1-yl)pyridine |
| Compound 45 | 3-(p-tolyl)thiophene | CH₃CH₂– | propylphenyl | 3-(but-1-yn-1-yl)pyridine |
| Compound 46 | 3-(m-tolyl)thiophene | CH₃CH₂– | propylphenyl | 3-(but-1-yn-1-yl)pyridine |
| Compound 47 | 2-methyl-1-(p-tolyl)-1H-imidazo[4,5-c]pyridine | CH₃CH₂– | propylphenyl | 3-(pent-1-yn-1-yl)pyridine |
| Compound 48 | 2-methyl-1-(p-tolyl)-1H-imidazo[4,5-c]pyridine | CH₃CH₂– | 1,1-diphenylpropyl | 3-(pent-1-yn-1-yl)pyridine |

TABLE 8

| Compound | R₁ | R₂ | R₃ | R₄ |
|---|---|---|---|---|
| Compound 49 | 1-(3-methylphenyl)-2-methyl-imidazo[4,5-c]pyridine | ethyl | propylphenyl | pent-2-ynyl-(pyridin-3-yl) |
| Compound 50 | 1-(4-methylphenyl)-2-isopropyl-imidazo[4,5-c]pyridine | ethyl | propylphenyl | pent-2-ynyl-(pyridin-3-yl) |
| Compound 51 | 1-(4-methylphenyl)-2-methyl-imidazo[4,5-b]pyridine | ethyl | propylphenyl | but-2-ynyl-(pyridin-3-yl) |
| Compound 52 | 1-(4-methylphenyl)-2-methyl-imidazo[4,5-b]pyridine | ethyl | hexyl | but-2-ynyl-(pyridin-3-yl) |
| Compound 53 | pyridin-3-yl | ethyl | (E)-propenylphenyl | but-2-ynyl-(pyridin-3-yl) |
| Compound 54 | 1-(4-methylphenyl)-benzimidazol-1-yl | ethyl | (E)-propenylphenyl | but-2-ynyl-(pyridin-3-yl) |
| Compound 55 | 1-(4-methylphenyl)-imidazol-1-yl | ethyl | propylphenyl | 3-methyl-but-1-ynyl-(pyridin-3-yl) |

TABLE 8-continued
| Compound | R₁ | R₂ | R₃ | R₄ |
|---|---|---|---|---|
| Compound 56 | 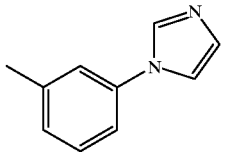 | CH₃ | 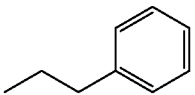 | 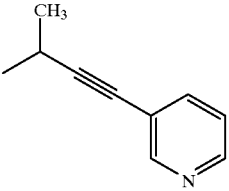 |
TABLE 9
| Compound | R₁ | R₂ | R₃ | R₄ |
|---|---|---|---|---|
| Compound 57 | 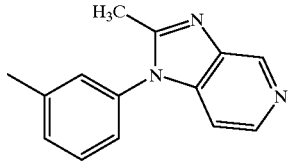 | CH₃ |  | 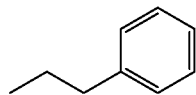 |
| Compound 58 | 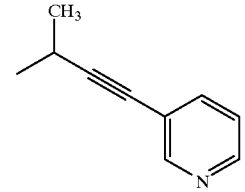 | CH₃ | 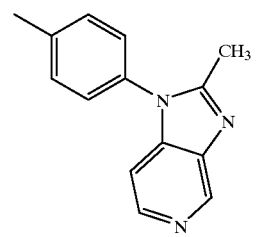 |  |
| Compound 59 | 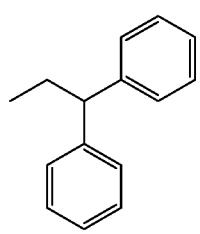 | CH₃ | 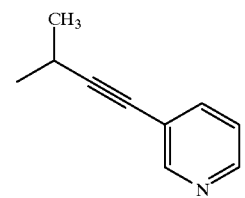 | 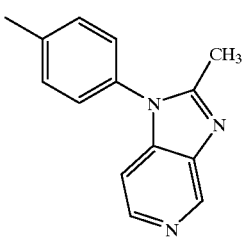 |
| Compound 60 |  | CH₃ | 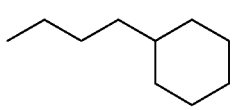 | 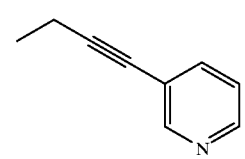 |

TABLE 9-continued

| Compound | R₁ | R₂ | R₃ | R₄ |
| --- | --- | --- | --- | --- |
| Compound 61 | 1-(4-methylphenyl)-2-methyl-imidazo[4,5-c]pyridine | CH₃CH₂CH₂- | 1,1-diphenylpropenyl | 3-pyridyl-butynyl |
| Compound 62 | 1-(4-methylphenyl)-2-methyl-imidazo[4,5-c]pyridine | CH₃CH₂CH₂- | 2-methoxy-5-propyl-phenoxy-methyl-cyclopentane | 3-pyridyl-butynyl |
| Compound 63 | 1-(4-methylphenyl)-2-methyl-imidazo[4,5-c]pyridine | CH₃CH₂CH₂- | 2-methoxy-5-propyl-phenoxy-ethyl-(4-fluorophenyl) | 3-pyridyl-butynyl |
| Compound 64 | 1-(4-methylphenyl)-2-methyl-imidazo[4,5-c]pyridine | CH₃CH₂CH₂- | 2-methoxy-5-propyl-phenoxy-ethyl-(4-methylthiazol-5-yl) | 3-pyridyl-butynyl |

TABLE 10

| Compound | R₁ | R₂ | R₃ | R₄ |
| --- | --- | --- | --- | --- |
| Compound 65 | 1-(4-methylphenyl)-2-methyl-imidazo[4,5-c]pyridine | CH₃CH₂CH₂- | 2-ethyl-indanyl | 3-pyridyl-butynyl |

TABLE 10-continued

| Compound | R₁ | R₂ | R₃ | R₄ |
|---|---|---|---|---|
| Compound 66 | | | | |
| Compound 67 | | | | |
| Compound 68 | | | | |
| Compound 69 | | | | |
| Compound 70 | | | | |
| Compound 71 | | | | |

TABLE 10-continued

| Compound | R₁ | R₂ | R₃ | R₄ |
| --- | --- | --- | --- | --- |
| Compound 72 | 2-methyl-1-(m-tolyl)-1H-imidazo[4,5-c]pyridine | propyl | 1,1-diphenylpropyl | but-1-ynyl-pyridin-3-yl |

TABLE 11

| Compound | R₁ | R₂ | R₃ | R₄ |
| --- | --- | --- | --- | --- |
| Compound 73 | 2-methyl-1-(m-tolyl)-1H-imidazo[4,5-c]pyridine | propyl | propylphenyl | but-1-ynyl-pyridin-3-yl |
| Compound 74 | 2-trifluoromethyl-1-(m-tolyl)-1H-imidazo[4,5-c]pyridine | propyl | propylphenyl | but-1-ynyl-pyridin-3-yl |
| Compound 75 | 2-methyl-1-(p-tolyl)-1H-imidazo[4,5-c]pyridine | propyl | 3-(trifluoromethyl)-propylphenyl | but-1-ynyl-pyridin-3-yl |
| Compound 76 | 2-methyl-1-(p-tolyl)-1H-imidazo[4,5-c]pyridine | propyl | 4-isopropyl-propylphenyl | but-1-ynyl-pyridin-3-yl |
| Compound 77 | 2-methyl-1-(p-tolyl)-1H-imidazo[4,5-c]pyridine | propyl | propylnaphthalenyl | but-1-ynyl-pyridin-3-yl |

TABLE 11-continued

| Compound | $R_1$ | $R_2$ | $R_3$ | $R_4$ |
|---|---|---|---|---|
| Compound 78 | 4-methylphenyl-2-methyl-imidazo[4,5-c]pyridinyl | ethyl (CH₂CH₃) | 1-(4-fluorophenyl)-1-(4-fluorophenyl)propyl | 3-pyridinyl-propynyl |
| Compound 79 | 4-methylphenyl-2-methyl-imidazo[4,5-c]pyridinyl | ethyl (CH₂CH₃) | 3-phenylpropyl | 3-pyridinyl-propynyl |
| Compound 80 | 4-methylphenyl-2-methyl-imidazo[4,5-c]pyridinyl | ethyl (CH₂CH₃) | 5-phenylpentyl | 3-pyridinyl-propynyl |

Preparation Examples

Example 81 (Preparation of Tablets)

| | |
|---|---|
| Present Compound (Compound 1) | 25 g |
| Lactose | 62 g |
| Corn starch | 40 g |
| Hydroxypropylcellulose | 2 g |
| Magnesium stearate | 1 g |

The present compound (i.e., Compound 1), lactose, and corn starch were mixed until becoming homogeneous, then a 5 w/v % ethanol solution of hydroxypropylcellulose was added and the mixture kneaded and granulated. The granules were passed through a 16 mesh sieve to standardize their size, then form to tablets by an ordinary method to obtain tablets of a weight per tablet of 130 mg, a diameter of 7 mm, and a content of the main drug of 25 mg.

Test Examples

Test Example 1

In Vitro Test of Action Suppressing Proliferation of Cancer Cells combined administration of Doxorubicin Human rhinopharynx cancer derived KB cells (i.e., sensitive cells) and their multi-drug resistant clone KB/VJ 300 cells (i.e., resistant cells) were used as the test cells. As the incubation solutions, use was made of 10% fetal calf serum (Flow Laboratories) and Eagle MEM medium (Nissui Seiyaku) containing 0.292 mg/ml of L-glutamine (Flow Laboratories). The tests of the action for overcoming resistance to anti-cancer drugs or action for increasing the effect of the anti-cancer drug with the combined administration of the anti-cancer drug doxorubicin (i.e., adriamycin, ADM) and the test compound were performed as follows:

The test cells were suspended in incubation solutions and adjusted to a cell density of about 200 cells/ml. The cell suspensions were injected in 2 ml amounts into petri dishes and were incubated in a $CO_2$ gas incubator (5% $CO_2$, 95% air) at 37° C. for 24 hours. Then, 5–10 μl of a predetermined concentration of the aqueous ADM solution and a predetermined concentration of a DMSO solution of the test compound were added, then the incubation was continued for a further 6 days. After the end of the incubation, the result was immobilized with methanol, Tripan blue stained and measured for the number of colonies per dish. The results were used to prepare a volume-reaction curve. From this, the ADM concentration of the 50% cell survival rate ($LD_{50}$) was calculated and the effect for overcoming resistance to anti-cancer drugs and the effect for increasing the effect of anti-cancer drugs were judged. The results are shown in Table 12 to Table 14 using the concentration of $LD_{50}$ of ADM in the ADM alone group when KB cells were used as the resistance degree 1 and calculating the resistances of the following $LD_{50}$ concentrations as relative ratios. In the tables, "ADM alone (control)" shows the group administered just ADM, "ADM+Compound 1" shows the group combined administration of the ADM and the Compound 1

(1 μg/ml) and, similarly below, "ADM+Compound 80" shows the group combined administration of the ADM and the Compound 80 (1 μg/ml).

TABLE 12

| | Degree of resistance for ADM | |
|---|---|---|
| | KB | VJ-300 |
| ADM alone (control) | 1.00 | 12.9–33.5 |
| ADM + Compound 1 | 1.01 | 4.76 |
| ADM + Compound 2 | 0.45 | 1.12 |
| ADM + Compound 3 | 0.54 | 0.96 |
| ADM + Compound 4 | 1.01 | 1.12 |
| ADM + Compound 5 | 0.39 | 1.37 |
| ADM + Compound 6 | 0.70 | 2.06 |
| ADM + Compound 7 | 0.82 | 1.38 |
| ADM + Compound 8 | 0.41 | 1.38 |
| ADM + Compound 9 | 0.50 | 1.20 |
| ADM + Compound 10 | 1.06 | 1.14 |
| ADM + Compound 11 | 0.47 | 0.91 |
| ADM + Compound 12 | 0.44 | 1.01 |
| ADM + Compound 13 | 0.41 | 1.02 |
| ADM + Compound 14 | 0.46 | 0.92 |
| ADM + Compound 15 | 0.48 | 0.78 |
| ADM + Compound 16 | 0.35 | 1.02 |
| ADM + Compound 17 | 0.96 | 1.04 |
| ADM + Compound 18 | 0.48 | 0.99 |
| ADM + Compound 19 | 0.55 | 1.08 |
| ADM + Compound 20 | 0.71 | 1.03 |
| ADM + Compound 21 | 0.51 | 1.05 |
| ADM + Compound 22 | 1.14 | 2.30 |
| ADM + Compound 23 | 1.04 | 2.53 |
| ADM + Compound 24 | 0.84 | 1.42 |

TABLE 13

| | Degree of resistance for ADM | |
|---|---|---|
| | KB | VJ-300 |
| ADM alone (control) | 1.00 | 26.6–35.6 |
| ADM + Compound 25 | 0.40 | 1.04 |
| ADM + Compound 26 | 0.89 | 1.11 |
| ADM + Compound 27 | 0.43 | 1.09 |
| ADM + Compound 28 | 1.09 | 2.47 |
| ADM + Compound 29 | 0.81 | 2.25 |
| ADM + Compound 30 | 0.57 | 1.10 |
| ADM + Compound 31 | 0.48 | 1.10 |
| ADM + Compound 32 | 0.78 | 1.26 |
| ADM + Compound 33 | 1.01 | 1.40 |
| ADM + Compound 34 | 1.00 | 1.12 |
| ADM + Compound 35 | 1.00 | 1.07 |
| ADM + Compound 36 | 1.08 | 1.15 |
| ADM + Compound 37 | 1.22 | 1.24 |
| ADM + Compound 38 | 1.06 | 1.74 |
| ADM + Compound 39 | 1.01 | 7.28 |
| ADM + Compound 40 | 1.02 | 1.27 |
| ADM + Compound 41 | 0.70 | 1.33 |
| ADM + Compound 42 | 0.74 | 1.44 |
| ADM + Compound 43 | 0.84 | 1.52 |
| ADM + Compound 44 | 0.87 | 3.81 |
| ADM + Compound 45 | 0.98 | 1.15 |
| ADM + Compound 46 | 1.10 | 3.53 |
| ADM + Compound 47 | 0.49 | 1.06 |
| ADM + Compound 48 | 0.94 | 1.09 |
| ADM + Compound 49 | 0.45 | 1.22 |
| ADM + Compound 50 | 0.53 | 1.35 |
| ADM + Compound 51 | 0.67 | 1.43 |
| ADM + Compound 52 | 1.18 | 1.60 |

TABLE 14

| | Degree of resistance for ADM | |
|---|---|---|
| | KB | VJ-300 |
| ADM alone (control) | 1.00 | 26.6–42.2 |
| ADM + Compound 53 | 0.94 | 4.08 |
| ADM + Compound 54 | 0.82 | 0.97 |
| ADM + Compound 55 | 0.82 | 3.23 |
| ADM + Compound 56 | 0.48 | 1.12 |
| ADM + Compound 57 | 0.39 | 1.01 |
| ADM + Compound 58 | 0.81 | 1.17 |
| ADM + Compound 59 | 0.67 | 1.10 |
| ADM + Compound 60 | 1.13 | 1.29 |
| ADM + Compound 61 | 0.71 | 0.94 |
| ADM + Compound 62 | 0.55 | 1.44 |
| ADM + Compound 63 | 0.72 | 1.39 |
| ADM + Compound 64 | 0.49 | 2.64 |
| ADM + Compound 65 | 0.89 | 1.19 |
| ADM + Compound 66 | 0.51 | 1.18 |
| ADM + Compound 67 | 0.63 | 1.37 |
| ADM + Compound 68 | 0.37 | <0.65 |
| ADM + Compound 69 | 0.39 | <0.65 |
| ADM + Compound 70 | 0.52 | 1.22 |
| ADM + Compound 71 | 0.83 | 1.14 |
| ADM + Compound 72 | 0.B0 | 1.30 |
| ADM + Compound 73 | 0.34 | 0.98 |
| ADM + Compound 74 | 0.62 | 1.16 |
| ADM + Compound 75 | 0.65 | 1.49 |
| ADM + Compound 76 | 0.62 | 1.78 |
| ADM + Compound 77 | 0.66 | 0.84 |
| ADM + Compound 78 | 0.59 | 1.62 |
| ADM + Compound 79 | 0.65 | 1.22 |
| ADM + Compound 80 | 0.58 | 1.87 |

Test Example 2

In Vitro Test of Action Suppressing Proliferation of Cancer Cells by Combined Administration of Vincristine The same method as in Test Example 1 was used to test the action of vincristine (VCR) on anti-cancer drugs, prepare a volume-reaction curve, and calculate the resistances. The results are shown in Table 15. In Table 15, "VCR alone (control)" shows the group administered with VCR alone, "VCR +Compound 3" shows the group combined administration of VCR and the Compound 3 (1 μg/ml), and, the following similarly, "VCR +Compound 22" indicates the group combined administration of VCR and the Compound 22 (1 μg/ml).

TABLE 15

| | Degree of resistance for VCR | |
|---|---|---|
| | KB | VJ-300 |
| VCR alone (control) | 1.00 | 903–970 |
| VCR + Compound 3 | 0.39 | 1.74 |
| VCR + Compound 4 | 0.33 | 2.73 |
| VCR + Compound 6 | 0.20 | 2.87 |
| VCR + Compound 7 | 0.22 | 3.46 |
| VCR + Compound 15 | 0.36 | 2.66 |
| VCR + Compound 17 | 0.34 | 2.64 |
| VCR + Compound 22 | 0.63 | 2.43 |

Test Example 3

In Vivo Test of Action Suppressing Proliferation of Cancer Cells by Combined Administration of Anti-cancer Drug Etoposide Effect of Overcoming Resistance to an Anti-cancer Drug for VCR Resistant Murine Leukemia Cell Bearing Mice $1.2 \times 10^5$ VCR resistant murine leukemia (P388/VCR) cells were transplanted intravenously into groups of 5–6 $CDF_1$ female mice, then the compound of the present invention (20 mg/kg) and Etoposide (VP-16) (3 mg/kg) were administered intravenously once per day for 5 days, after dissolving them in a physiological salt solution containing a small amount of hydrochloric acid. The observation was started from the next day. The number of survival days were found and the life prolonging rate (T/C) with respect to the controls was found. The effect in overcoming resistance to an anti-cancer drug (T/V) was found by the following formula. The results are shown in Table 16 to Table 22. In the Tables, "control" shows the group not administered anything, "VP-16 alone" shows the group administered VP-16 (3 mg/kg), "VP-16 +Compound 1" shows the group combined administration of VP-16 (3 mg/kg) and the Compound 1 (20 mg/kg) and, similarly after this, "VP-16+ Compound No" shows the group combined administration of the VP-16 (3 mg/kg) and the Compound No. (20 mg/kg).

Effect of overcoming resistance to the anti-cancer drug (T/V) %

=[(Rate of prolongation of life using VP-16 and the present compound (T/C))/(Rate of prolongation of life using VP-16 alone (T/C))]×100

TABLE 16

| | Average days of survival (day) | Rate of prolongation of life T/C (%) | Effect of overcoming resistance T/V (%) |
|---|---|---|---|
| Control | 9.2 | 100 | — |
| VP-16 alone | 9.5 | 103 | 100 |
| VP-16 + Compound 1 | 13.6 | 148 | 143 |
| VP-16 + Compound 4 | 14.8 | 161 | 156 |
| VP-16 + Compound 6 | 16.0 | 174 | 168 |
| VP-16 + Compound 7 | 13.4 | 146 | 141 |
| VP-16 + Compound 9 | 15.0 | 163 | 158 |
| VP-16 + Compound 10 | 17.0 | 185 | 179 |
| VP-16 + Compound 17 | 13.4 | 146 | 141 |
| VP-16 + Compound 22 | 14.6 | 159 | 154 |
| VP-16 + Compound 23 | 15.8 | 172 | 166 |

TABLE 17

| | Average days of survival (day) | Rate of prolongation of life T/C (%) | Effect of overcoming resistance T/V (%) |
|---|---|---|---|
| Control | 10.2 | 100 | — |
| VP-16 alone | 11.0 | 108 | 100 |
| VP-16 + Compound 11 | 15.8 | 155 | 144 |
| VP-16 + Compound 12 | 16.8 | 165 | 153 |
| VP-16 + Compound 13 | 15.7 | 154 | 143 |
| VP-16 + Compound 14 | 15.7 | 154 | 143 |
| VP-16 + Compound 16 | 15.0 | 147 | 136 |
| VP-16 + Compound 18 | 16.0 | 157 | 145 |
| VP-16 + Compound 19 | 16.0 | 157 | 145 |
| VP-16 + Compound 20 | 14.7 | 144 | 134 |

TABLE 18

| | Average days of survival (day) | Rate of prolongation of life T/C (%) | Effect of overcoming resistance T/V (%) |
|---|---|---|---|
| Control | 9.7 | 100 | — |
| VP-16 alone | 10.2 | 105 | 100 |
| VP-16 + Compound 25 | 12.8 | 132 | 125 |
| VP-16 + Compound 27 | 12.8 | 132 | 125 |
| VP-16 + Compound 30 | 13.5 | 139 | 132 |
| VP-16 + Compound 31 | 13.8 | 142 | 135 |
| VP-16 + Compound 73 | 16.2 | 167 | 159 |
| VP-16 + Compound 74 | 13.0 | 134 | 127 |

TABLE 19

| | Average days of survival (day) | Rate of prolongation of life T/C (%) | Effect of overcoming resistance T/V (%) |
|---|---|---|---|
| Control | 10.2 | 2100 | — |
| VP-16 alone | 10.8 | 106 | 100 |
| VP-16 + Compound 26 | 13.8 | 135 | 128 |
| VP-16 + Compound 33 | 13.5 | 132 | 125 |
| VP-16 + Compound 49 | 14.8 | 145 | 137 |
| VP-16 + Compound 50 | 15.8 | 155 | 146 |
| VP-16 + Compound 55 | 13.5 | 132 | 125 |
| VP-16 + Compound 62 | 14.3 | 140 | 132 |
| VP-16 + Compound 63 | 14.3 | 140 | 132 |
| VP-16 + Compound 70 | 14.8 | 145 | 137 |

TABLE 20

| | Average days of survival (day) | Rate of prolongation of life T/C (%) | Effect of overcoming resistance T/V (%) |
|---|---|---|---|
| Control | 10.3 | 100 | — |
| VP-16 alone | 10.5 | 102 | 100 |
| VP-16 + Compound 47 | 15.2 | 148 | 145 |
| VP-16 + Compound 60 | 16.3 | 158 | 155 |
| VP-16 + Compound 66 | 14.5 | 141 | 138 |
| VP-16 + Compound 67 | 14.3 | 139 | 136 |

TABLE 21

| | Average days of survival (day) | Rate of prolongation of life T/C (%) | Effect of overcoming resistance T/V (%) |
|---|---|---|---|
| Control | 10.3 | 100 | — |
| VP-16 alone | 11.0 | 107 | 100 |
| VP-16 + Compound 48 | 14.3 | 139 | 130 |
| VP-16 + Compound 58 | 14.7 | 143 | 134 |
| VP-16 + Compound 65 | 16.0 | 155 | 145 |
| VP-16 + Compound 71 | 23.5 | 228 | 214 |
| VP-16 + Compound 72 | 15.5 | 150 | 141 |

TABLE 22

| | Average days of survival (day) | Rate of prolongation of life T/C (%) | Effect of overcoming resistance T/V (%) |
|---|---|---|---|
| Control | 10.2 | 100 | — |
| VP-16 alone | 10.8 | 106 | 100 |
| VP-16 + Compound 56 | 14.2 | 139 | 131 |
| VP-16 + Compound 57 | 15.0 | 147 | 139 |
| VP-16 + Compound 59 | 14.8 | 145 | 137 |
| VP-16 + Compound 61 | 15.7 | 154 | 145 |
| VP-16 + Compound 69 | 17.5 | 172 | 162 |

Test Example 4

In Vivo Test of Action Suppressing Proliferation of Cancer Cells by Combined Administration of Anti-Cancer Drug Etoposide The Test Example 3 was repeated using 10 mg/kg administration of the present compound and the effects of overcoming resistance to the anti-cancer drug were determined from the average days of survival. The results are shown in Table 23.

TABLE 23

| | Average days of survival (day) | Rate of prolongation of life T/C (%) | Effect of overcoming resistance T/V (%) |
|---|---|---|---|
| Control | 10.4 | 100 | — |
| VP-16 alone | 10.6 | 102 | 100 |
| VP-16 + Compound 23 | 13.0 | 125 | 123 |
| VP-16 + Compound 71 | 17.4 | 167 | 164 |
| VP-16 + Compound 78 | 14.2 | 137 | 134 |

Test Example 5

Action Easing KCl Contraction in Rat Arteries

An approximately 2 mm long ring specimen was taken from the thoracic aorta of the rat and suspended in a Magnus tube filled with Krebs solution of 37° C. aerated with 95% $O_2$–5% $CO_2$. The specimen was stabilized for approximately 60 minutes, then a potassium chloride solution was added to the Magnus tube to give a final concentration of 50 mM. The positive control compound or the compound of the present invention was cumulatively added to become $1 \times 10^{-6}$M when the contraction reaction occurring at that time reached equilibrium. The contraction force was recorded by an FD-pickup (Nihon Koden) via a polygraph (Nihon Koden). The results are shown in Table 24 as the inhibitory rate of hyperpotassium contraction at $10^{-6}$M, together with the results of the positive control compounds, Nicardipine and Verapamil.

TABLE 24

| Positive control compound and invention compound | Inhibitory Rate (%) at $10^{-6}$M |
|---|---|
| Nicardipine | 100 |
| Verapamil | 42.3 |
| Compound 1 | 0 |
| Compound 6 | 7.5 |
| Compound 14 | 0 |

TABLE 24-continued

| Positive control compound and invention compound | Inhibitory Rate (%) at $10^{-6}$M |
|---|---|
| Compound 16 | 0 |
| Compound 17 | 0 |
| Compound 22 | 0 |

Test Example 6

Acute Toxicity Test

Animals used: ddY male mice (SLC Japan), 4–5 weeks old, three to five mice per group.

Test method: The compound of the present invention was suspended in 0.5% sodium carboxymethylcellulose (CMC-Na) containing 0.1% Tween 80. It was administered to the mice intraperitoneally in amounts of 250, 500 or 1000 mg/kg in groups of three to five mice. The survival of the animals was observed up until 7 days after administration and $LD_{50}$ value was calculated according to a Probit method.

The test results are shown below:

| | $LD_{50}$ value |
|---|---|
| Compound 9 | >1000 mg/kg |
| Compound 22 | >1000 mg/kg |
| Compound 24 | >1000 mg/kg |

INDUSTRIAL APPLICABILITY

The 1,4-dihydropyridine derivative according to the present invention reverses the action of anti-cancer drugs when used in combination. The effects are particularly remarkable against cells acquiring resistance to anti-cancer drugs. For example, as clear from the above Table 15, human rhinopharynx cancer derived KB cell multi-drug resistant clone VJ-300 cells, compared with cells not acquiring resistance, required use of 903 to 970 times the concentration of the anti-cancer drug to obtain the same effect (50% cell survival rate), while with the combined use of the Compound 3 of the present invention (1 μg/ml), the same effect was obtained with 1.74 times the concentration.

Further, the compound according to the present invention is low in toxicity and exhibits its effects in tests both in vitro and in vivo, and therefore, is useful as a drug for overcoming resistance to an anti-cancer drug or a drugs for increasing the effect of an anti-cancer drug.

What is claimed is:

1. A compound having the formula (I):

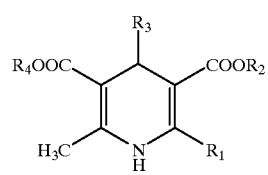

wherein $R_1$ represents a phenyl or pyridyl group, wherein the phenyl or pyridyl group is optionally substituted with a $C_1$ to $C_3$ lower alkylthio group, a $C_1$ mto $C_3$ lower alkyloxy group, a $C_1$ to $C_3$ lower alkyl group, a halogen atom, or a heterocyclic group selected from the group consisting of imidzaopyridine, piperazine, imidazole, morphoine, indole, benzimidazole, indazole, thiophene, and 1H-benzotriazole, wherein the heterocyclic group is optionally substituted with a $C_1$ to $C_3$ lower alkyl group, a trifluoromethyl group, or a halogen atom;

$R_2$ represents a $C_1$ to $C_5$ lower alkyl group;

$R_3$ represents a $C_1$ to $C_8$ alkyl, alkenyl or alkynyl group; a $C_3$ to $C_7$ cycloalkyl or cycloalkenyl group; or a $C_1$ to $C_4$ lower alkyl group or $C_2$ to $C_3$ lower alkenyl group substituted with a phenyl, thienyl, furyl, cyclohexyl, naphthyl, indanyl, 1,1a,6,10b-tetrahydrodibenzo[a,e]-cyclopropac[c]ycloheptene-yl, 5H-dibenzo[a,d] cycloheptene-yl group or 10,11-dihydro-5H-dibenzo[a,d]cyclohepten-yl ring group, wherein the ring group is optionally substituted with a halogen atom, $C_1$ to $C_3$ lower alkyloxy group, or a $C_1$ to $C_3$ lower alkyloxy group substituted with a cycloalkyl or phenyl group;

$R_4$ represents —A—$R_5$, wherein A represents a $C_3$ to $C_5$ alkynylene group having one triple bond; and $R_5$ represents a pyridyl, quinolyl, isoquinolyl or pyrimidyl group, each of which may be optionally substituted with a $C_1$ to $C_3$ lower alkyl group, $C_1$ to $C_3$ lower alkoxy group, or a halogen atom.

2. A compound as claimed in claim 1, wherein $R_1$ is a pyridyl group, or a phenyl group substituted with one heterocyclic group selected from the group consisting of imidazopyridine, piperazine, imidazole, morpholine, indole, benzimidazole, indazole, thiophene, and 1H-benzotriazole, provided that these heterocyclic groups may be substituted with a $C_1$ to $C_3$ lower alkyl group or trifluoromethyl group, $R_3$ is a $C_1$ to $C_6$ alkyl or alkenyl group; a $C_1$ to $C_4$ lower alkyl group or $C_2$ to $C_3$ lower alkenyl group substituted with a phenyl, thienyl, furyl, cyclohexyl, naphthyl, indanyl, 1,1a, 6,10b-tetrahydrodibenzo[a,e]cyclopropa[c]cycloheptene-yl, 5H-dibenzo[a,d]cycloheptene-yl group or 10,11-dihydro-5H-dibenzo[a,d]cyclohepten-yl group, provided that these groups may be substituted with a halogen atom, $C_1$ to $C_3$ lower alkyl, trifluoromethyl, substituted or unsubstituted $C_1$ to $C_3$ lower alkyloxy group; or a $C_5$ to $C_7$ cycloalkyl group.

3. A compound as claimed in claim 1, wherein $R_1$ is (2-substituted imidazo[4,5-c]pyridin-1-yl)phenyl group substituted, at the 2-position of the imidazo[4,5-c]pyridine, with a $C_1$ to $C_3$ lower alkyl or trifluoromethyl group, or a (1-imidazolyl)phenyl group.

4. A compound as claimed in claim 1, wherein $R_2$ is a methyl group, or ethyl group.

5. A compound as claimed in claim 1, wherein $R_3$ is a $C_1$ to $C_6$ alkyl or alkenyl group; a $C_1$ to $C_4$ lower alkyl group or a $C_2$ to $C_3$ lower alkenyl group, substituted with a thienyl or phenyl group, provided that the phenyl group may be substituted with a halogen atom, $C_1$ to $C_3$ lower alkyl, trifluoromethyl, $C_1$ to $C_3$ lower alkyloxy group, or a $C_1$ to $C_3$ lower alkyloxy group substituted with a cycloalkyl or phenyl group; or a cyclohexyl group.

6. A compound as claimed in claim 1, wherein $R_5$ is a 3-pyridyl,3-quinolyl, 4-isoquinolyl or 5-pyrimidyl group, provided that these groups may be substituted with a $C_1$ to $C_3$ lower alkyl group, $C_1$ to $C_3$ lower alkyloxy group, or a halogen atom.

7. A compound as claimed in claim 1, wherein A is a propynylene, 1-methyl-2-propynylene, or 2-butynylene group, and $R_5$ is a 3-pyridyl, 3-quinolyl, 4-isoquinolyl or 5-pyrimidyl group.

8. A pharmaceutical composition comprising a 1,4-dihydropyridine derivative according to claim 1 or its pharmacologically acceptable salt or hydrate and a carrier.

9. A method for overcoming resistance to an anti-cancer drug in a patient comprising administering to the patient a pharmaceutically effective amount of a compound according to claim 1 or its pharmacologically acceptable salt or hydrate.

10. A method for increasing the effect of an anti-cancer drug in a patient comprising administering to the patient a pharmaceutically effective a compound according to claim 1 or its pharmacologically acceptable salt or hydrate.

* * * * *